US011110279B2

(12) United States Patent
Roberts et al.

(10) Patent No.: US 11,110,279 B2
(45) Date of Patent: Sep. 7, 2021

(54) SIGNAL TRANSMISSION OPTIMIZATION FOR TISSUE CONDUCTION COMMUNICATION

(71) Applicant: Medtronic, Inc., Minneapolis, MN (US)

(72) Inventors: Jonathan P. Roberts, Coon Rapids, MN (US); Michael T. Hemming, Kiowa, CO (US); David J. Peichel, Minneapolis, MN (US); James D. Reinke, Maple Grove, MN (US); Michael B. Terry, Camas, WA (US)

(73) Assignee: Medtronic, Inc., Minneapolis, MN (US)

( * ) Notice: Subject to any disclaimer, the term of this patent is extended or adjusted under 35 U.S.C. 154(b) by 176 days.

(21) Appl. No.: 16/202,418

(22) Filed: Nov. 28, 2018

(65) Prior Publication Data

US 2019/0160290 A1    May 30, 2019

Related U.S. Application Data

(60) Provisional application No. 62/591,800, filed on Nov. 29, 2017.

(51) Int. Cl.
*A61N 1/372* (2006.01)
*A61N 1/39* (2006.01)
(Continued)

(52) U.S. Cl.
CPC ..... *A61N 1/37217* (2013.01); *A61N 1/36507* (2013.01); *A61N 1/39622* (2017.08);
(Continued)

(58) Field of Classification Search
CPC .............. A61B 5/0028; A61N 1/37205; A61N 1/37217; A61N 1/37252; A61N 1/37254;
(Continued)

(56) References Cited

U.S. PATENT DOCUMENTS

| 4,987,897 A | 1/1991 | Funke |
| 5,025,808 A * | 6/1991 | Hafner ................. A61N 1/3727 600/509 |

(Continued)

OTHER PUBLICATIONS

Peichel et al., "Implantable Medical Device and Method to Minimize Artifact From Tissue Conduction Communication Transmission", U.S. Appl. No. 16/203,939, filed Nov. 29, 2018, 79 pages.
(Continued)

*Primary Examiner* — Carl H Layno
*Assistant Examiner* — Jane C Kalinock

(57) ABSTRACT

A device includes a tissue conduction communication (TCC) transmitter that generates a TCC signal including a carrier signal having a peak-to-peak amplitude and a carrier frequency cycle length including a first polarity pulse for a first half of the carrier frequency cycle length and a second polarity pulse opposite the first polarity pulse for a second half of the carrier frequency cycle length. Each of the first polarity pulse and the second polarity pulse inject a half cycle charge into a TCC pathway. The TCC transmitter starts transmitting the TCC signal with a starting pulse having a net charge that is half of the half cycle charge and transmits alternating polarity pulses of the carrier signal consecutively following the starting pulse.

19 Claims, 11 Drawing Sheets

(51) Int. Cl.
A61N 1/365 (2006.01)
H04B 13/00 (2006.01)
A61N 1/375 (2006.01)
A61B 5/00 (2006.01)
A61B 5/053 (2021.01)
A61N 1/362 (2006.01)

(52) U.S. Cl.
CPC .......... H04B 13/005 (2013.01); *A61B 5/0028* (2013.01); *A61B 5/053* (2013.01); *A61N 1/3621* (2013.01); *A61N 1/3727* (2013.01); *A61N 1/3756* (2013.01); *A61N 1/37205* (2013.01); *A61N 1/37288* (2013.01); *A61N 1/395* (2013.01)

(58) Field of Classification Search
CPC .............. A61N 1/3727; A61N 1/37288; H04B 13/005; H04L 4/008; H04L 27/04; H04L 27/06; H04L 27/18; H04L 27/205; H04L 27/2071; H04L 27/2075; H04L 27/2276; H04L 27/2331; H04L 27/2335; H04L 27/24
USPC ...................................... 607/32, 60
See application file for complete search history.

(56) References Cited

U.S. PATENT DOCUMENTS

| | | | |
|---|---|---|---|
| 5,591,214 A | 1/1997 | Lu | |
| 6,076,016 A | 6/2000 | Feierbach | |
| 6,115,636 A | 9/2000 | Ryan | |
| 7,542,800 B2 | 6/2009 | Libbus et al. | |
| 7,623,930 B2 | 11/2009 | Zeijlemaker et al. | |
| 7,912,537 B2 | 3/2011 | Lee et al. | |
| 8,041,418 B2 | 10/2011 | Giftakis et al. | |
| 8,055,345 B2 | 11/2011 | Li et al. | |
| 8,275,444 B2 | 9/2012 | Zeijlemaker et al. | |
| 8,412,352 B2 | 4/2013 | Griswold et al. | |
| 8,457,742 B2 | 6/2013 | Jacobson | |
| 8,720,276 B2 | 5/2014 | Kuhn et al. | |
| 8,738,126 B2 | 5/2014 | Craig | |
| 8,744,572 B1 | 6/2014 | Greenhut et al. | |
| 8,924,008 B2 | 12/2014 | Yuyama et al. | |
| 8,954,008 B2 | 2/2015 | Wang et al. | |
| 8,996,115 B2 | 3/2015 | Trier et al. | |
| 9,168,383 B2 | 10/2015 | Jacobson et al. | |
| 9,636,511 B2 | 5/2017 | Carney et al. | |
| 9,687,659 B2 | 6/2017 | Von Arx et al. | |
| 9,713,434 B2 | 7/2017 | Barak | |
| 9,757,570 B2 | 9/2017 | Maile et al. | |
| 2004/0011366 A1 | 1/2004 | Schulman et al. | |
| 2012/0109258 A1 | 5/2012 | Cinbis et al. | |
| 2012/0277600 A1 | 11/2012 | Greenhut | |
| 2012/0323099 A1 | 12/2012 | Mothilal et al. | |
| 2013/0253345 A1 | 9/2013 | Griswold et al. | |
| 2013/0324825 A1 | 12/2013 | Ostroff et al. | |
| 2014/0043146 A1* | 2/2014 | Makdissi | A61N 1/37288 340/10.33 |
| 2014/0052207 A1* | 2/2014 | Vijayagopal | A61N 1/372 607/9 |
| 2015/0057721 A1 | 2/2015 | Stahmann et al. | |
| 2015/0306375 A1 | 10/2015 | Marshall et al. | |
| 2015/0306410 A1 | 10/2015 | Marshall et al. | |
| 2016/0213937 A1 | 7/2016 | Reinke et al. | |
| 2016/0296760 A1 | 10/2016 | Sahabi et al. | |
| 2017/0173346 A1* | 6/2017 | Kane | A61N 1/37217 |

OTHER PUBLICATIONS

Reinke et al., "Tissue Conduction Communication for Implantable Medical Devices", U.S. Appl. No. 16/204,505, filed Nov. 29, 2018, 88 pages.

Peichel et al., "Tissue Conduction Communication in an Implantable Medical Device System", U.S. Appl. No. 16/204,172, filed Nov. 29, 2018, 92 pages.

Zhao et al, "Device, System and Method With Adaptive Timing for Tissue Conduction Communication Transmission", U.S. Appl. No. 16/220,093, filed Dec. 14, 2018, 65 pages.

(PCT/US2018/062730) PCT Notification of Transmittal of the International Search Report and the Written Opinion of the International Searching Authority, dated Mar. 11, 2019, 11 pages.

\* cited by examiner

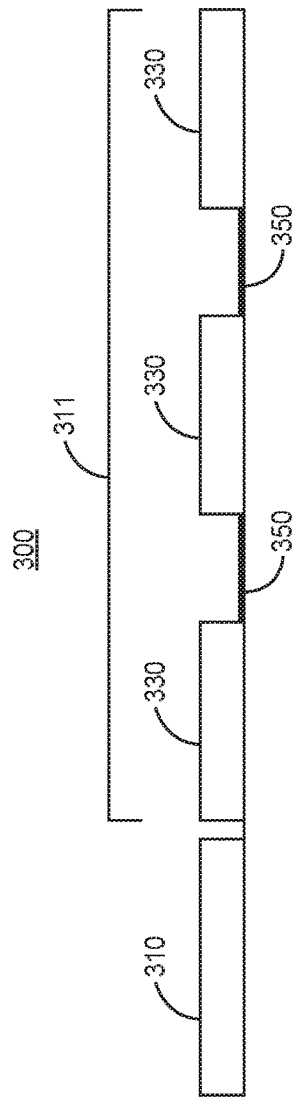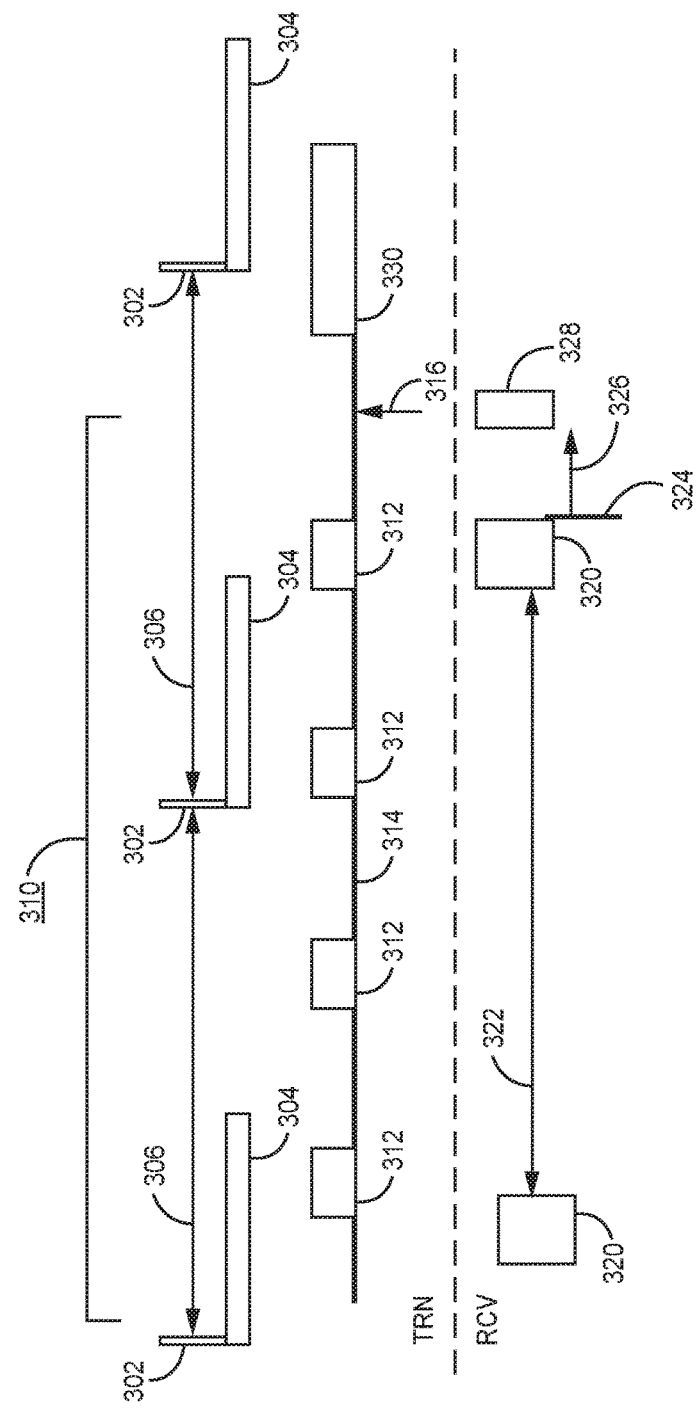

SIGNAL TRANSMISSION OPTIMIZATION FOR TISSUE CONDUCTION COMMUNICATION

TECHNICAL FIELD

The disclosure relates generally to devices, systems and methods for communicating using tissue conduction communication.

BACKGROUND

Communication between two or more devices associated with a person, e.g., implanted within the person and/or attached to or otherwise contacting the person, may be desirable in a number of applications, such as for monitoring or managing health of a patient. Communication between these devices may, for example, enable the exchange of information, coordinated monitoring of a health condition and/or coordinated therapy to treat health conditions. Such systems, some examples of which are described below, may communicate using tissue conduction communication (TCC). TCC uses the human body as the medium of communication. TCC may sometimes be referred to as human body conduction (HBC) or intrabody communication.

A wide variety of implantable medical devices (IMDs) for delivering a therapy to or monitoring a physiological condition of a patient have been used clinically or proposed for clinical use in patients. Examples include IMDs that deliver therapy to and/or monitor conditions associated with the heart, muscle, nerve, brain, stomach or other tissue. Some therapies include the delivery of electrical stimulation to such tissues. Some IMDs may employ electrodes for the delivery of therapeutic electrical signals to such organs or tissues, electrodes for sensing intrinsic physiological electrical signals within the patient, which may be propagated by such organs or tissue, and/or other sensors for sensing physiological signals of a patient.

Implantable cardioverter defibrillators (ICDs), for example, may be used to deliver high energy defibrillation and/or cardioversion shocks to a patient's heart when atrial or ventricular tachyarrhythmia, e.g., tachycardia or fibrillation, is detected. An ICD may detect a tachyarrhythmia based on an analysis of a cardiac electrogram sensed via electrodes, and may deliver anti-tachyarrhythmia shocks, e.g., defibrillation shocks and/or cardioversion shocks, via electrodes. An ICD or an implantable cardiac pacemaker, as another example, may provide cardiac pacing therapy to the heart when the natural pacemaker and/or conduction system of the heart fails to provide synchronized atrial and ventricular contractions at rates and intervals sufficient to sustain healthy patient function. ICDs and cardiac pacemakers may also provide overdrive cardiac pacing, referred to as anti-tachycardia pacing (ATP), to suppress or convert detected tachyarrhythmias in an effort to avoid cardioversion/defibrillation shocks.

Some IMDs are coupled to one or more of the electrodes used to sense electrical physiological signals and deliver electrical stimulation via one or more leads. A medical electrical lead carrying sensing and/or electrical therapy delivery electrodes allow the IMD housing to be positioned a location spaced apart from the target site for sensing and/or stimulation delivery. For example, a subcutaneously or sub-muscularly implanted housing of an ICD or implantable cardiac pacemaker may be coupled to endocardial electrodes via one or more medical electrical leads that extend transvenously to the patient's heart. Other ICD systems, referred to as extracardiovascular ICD systems, are not coupled to any transvenous leads, and instead sense and deliver shocks via electrodes implanted away from the patient's heart, e.g., implanted subcutaneously or substernally. The extra-cardiovascular electrodes may be provided along the housing of the subcutaneous ICD and/or coupled to the housing via one or more leads extending subcutaneously, submuscularly or substernally from the housing.

Leadless IMDs may also be used to deliver therapy to a patient, and/or sense physiological parameters of a patient. In some examples, a leadless IMD may include one or more electrodes on its outer housing to deliver therapeutic electrical stimulation to the patient, and/or sense intrinsic electrical signals of patient. For example, a leadless pacemaker may be used to sense intrinsic depolarizations or other physiological parameters of the patient, and/or deliver therapeutic electrical stimulation to the heart. A leadless pacemaker may be positioned within or outside of the heart and, in some examples, may be anchored to a wall of the heart via a fixation mechanism.

In some situations, two or more IMDs are implanted within a single patient. It may be desirable for the two or more IMDs to be able to communicate with each other, e.g., to coordinate, or cooperatively provide, sensing for monitoring the patient and/or therapy delivery. Although some IMDs communicate with other medical devices, e.g., with external programming devices, using radio-frequency (RF) telemetry, TCC allows for communication between two or more IMDs by transmitting signals between the electrodes of two IMDs via a conductive tissue pathway. Likewise, TCC may be utilized to communicate between an IMD and an external device having electrodes proximate to or in contact with the skin of the patient or between two external devices having electrodes proximate to or in contact with the skin of the patient.

SUMMARY

The techniques of this disclosure generally relate to optimized transmission of TCC signals by a device. The techniques of this disclosure are described in the context of an IMD. However, the techniques can be utilized by any device, medical or non-medical, implanted or external, that communicates using TCC. The TCC signals are transmitted and modulated in a manner that avoids or minimizes interference with electrical signal sensing circuitry of the transmitting IMD or another medical device. An IMD operating according to the techniques disclosed herein may control the cycle length and/or amplitude of a starting and ending pulse of a TCC signal to prevent direct current (DC) voltage shifts at a sensing electrode vector coupled to electrical signal sensing circuity. The IMD may modulate the carrier signal of a TCC signal using phase shift keying (PSK) by generating charge balanced phase shift pulses to avoid unbalanced phase shifts that may interfere with electrical signal sensing circuitry.

In one example, the disclosure provides a device comprising a housing and a tissue conduction communication (TCC) transmitter enclosed by the housing. The TCC transmitter is configured to transmit one or more TCC signals of a TCC communication session via a transmitting electrode vector. The device also includes a controller configured to control the TCC transmitter to generate a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length, transmit a starting pulse of the first one of the TCC signals having a net charge that is a fraction of the full cycle charge, the fraction being less than one-half, and transmit a first plurality of the alternating polarity pulses of the first TCC signal consecutively following the starting pulse, each one of the first plurality of alternating polarity pulses having a net charge of one-half of the full cycle charge.

In another example, the disclosure provides a method comprising generating a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length; transmitting a starting pulse of the first one of the TCC signals having a net charge that is a fraction of the full cycle charge, the fraction being less than one-half, and transmitting a first plurality of the alternating polarity pulses of the first TCC signal consecutively following the starting pulse, each one of the first plurality of alternating polarity pulses having a net charge of one-half of the full cycle charge.

In another example, the disclosure provides a non-transitory, computer-readable storage medium comprising a set of instructions which, when executed by a device having a tissue conduction communication (TCC) transmitter, cause the device to generate a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length; transmit a starting pulse of a first one of the TCC signals of a TCC communication session having a net charge that is between one-sixth and one-third of the full cycle charge, and transmit a first plurality of the alternating polarity pulses of the first TCC signal consecutively following the starting pulse, each one of the first plurality of alternating polarity pulses having a net charge of one-half of the full cycle charge.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 8 is a conceptual diagram of a portion of a TCC transmission session that may be executed by the TCC transmitter of FIG. 6.

FIG. 9 is a diagram of one example of operations performed during a wakeup mode by an IMD system according to one example.

DETAILED DESCRIPTION

Wireless communication between two or more medical devices may be desired for a number of reasons, including to exchange data and/or to coordinate, or cooperatively provide, sensing of physiological signals and/or therapy delivery. TCC signals may be wirelessly transmitted from one IMD to one or more IMDs co-implanted within a patient and/or to an external medical device having skin or surface electrodes coupled to the patient for transmitting and/or receiving TCC signals. Some IMDs and external medical devices may be configured to sense an electrophysiological signal via sensing electrodes and/or monitor electrical impedance such as transthoracic impedance signals. Examples of electrophysiological signals include a cardiac electrical signal produced by the patient's heart, an electromyogram signal produced by skeletal muscle tissue, and other electrophysiological signals produced by the brain, nerve or muscle tissue. Transmission of a communication signal may cause interference with electrical signal sensing circuitry. Transmission of a communication signal through body tissue may unintentionally cause electrical stimulation of muscle or nerves depending on the amplitude and frequency of the transmitted signal. TCC signal transmission techniques disclosed herein are provided to minimize the likelihood of interference with electrical signal sensing circuitry of an IMD system and minimize the likelihood of unintentionally stimulating muscle or nerve tissue.

An IMD or an external medical device that includes electrical signal sensing circuitry configured to receive an electrophysiological signal or monitor electrical impedance may be a TCC transmitting device, an intended TCC receiving device, or an unintended receiving device that is coupled to electrodes within the tissue conduction pathway of a TCC signal being transmitted between two other devices. In each case, a transmitted TCC signal may be received by sensing electrodes coupled to the transmitting or receiving IMD or an external device and interfere with the electrical signal sensing circuitry. In other examples, a transmitting or receiving device may be configured to monitor the electrical impedance of one or more medical electrical leads or the tissue impedance between one or more electrode vectors coupled to the device. A TCC transmitter and TCC transmission techniques are disclosed herein for minimizing the likelihood of a TCC signal interfering with electrophysiological signal sensing circuitry, impedance monitoring, or other monitoring of electrical signals performed by a system.

Figure 1:
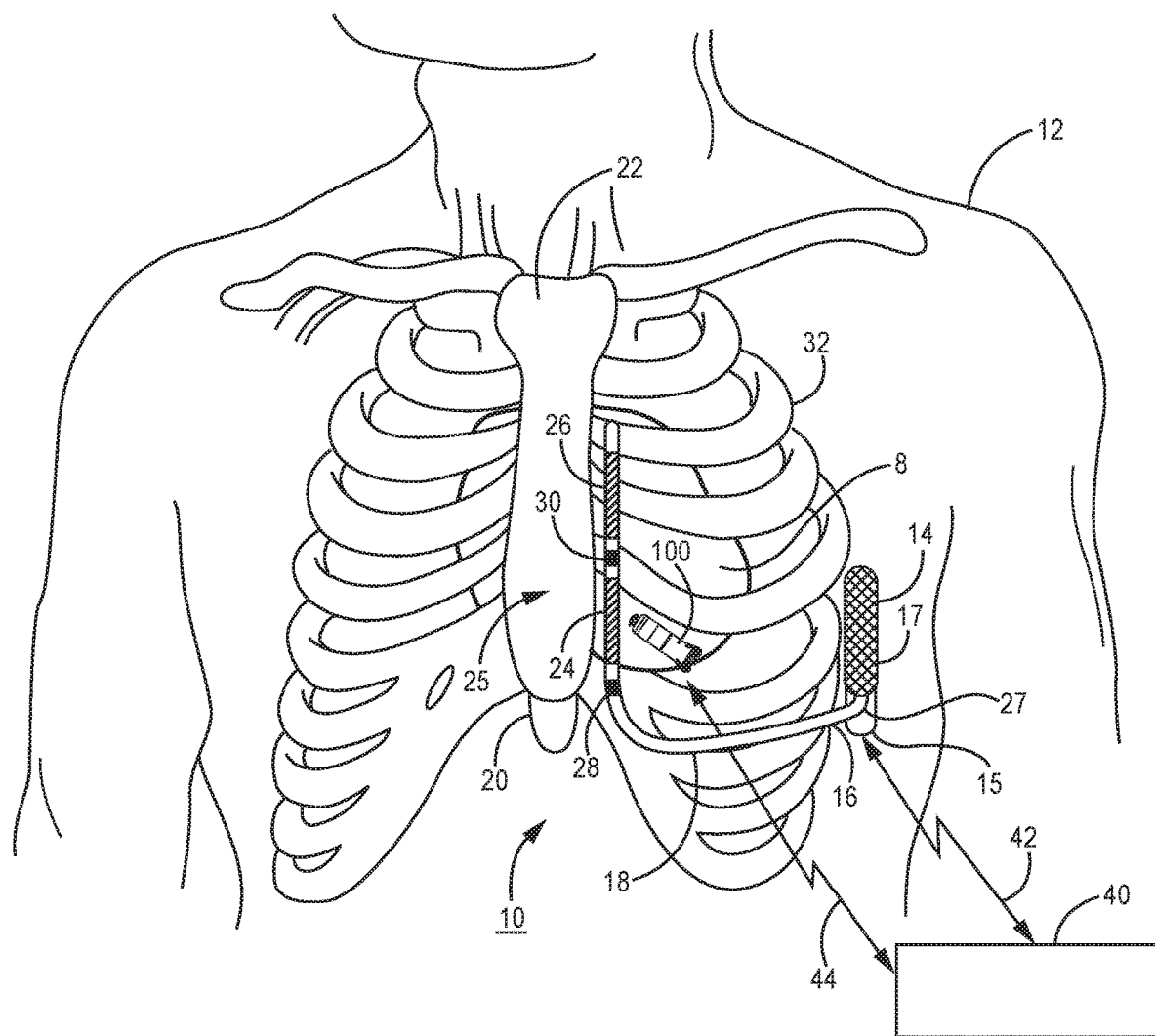
FIG. 1 is a conceptual diagram of an IMD system capable of TCC according to one example.

FIG. 1 is a conceptual diagram of an IMD system 10 capable of TCC according to one example. FIG. 1 is a front view of a patient 12 implanted with IMD system 10. IMD system 10 includes an ICD 14, an extra-cardiovascular electrical stimulation and sensing lead 16 coupled to ICD 14, and an intra-cardiac pacemaker 100. ICD 14 and pacemaker 100 may be enabled to communicate via TCC for transmitting a variety of data or commands. For example, ICD 14 and pacemaker 100 may be configured to communicate via TCC to confirm detected cardiac events or a detected heart rhythm and/or coordinate delivery of cardiac pacing pulses for bradycardia pacing, ATP therapy, cardioversion/defibrillation (CV/DF) shocks, post-shock pacing, cardiac resynchronization therapy (CRT) or other electrical stimulation therapies in response to an abnormal heart rhythm being detected by one or both of the IMDs 14 and 100.

IMD system 10 senses cardiac electrical signals, such as R-waves attendant to ventricular depolarizations and/or P-waves attendant to atrial depolarizations, for detecting abnormal heart rhythms with high sensitivity and specificity to enable IMD system 10 to deliver (or withhold) appropriate therapies at appropriate times. Transmission of TCC signals by an IMD, e.g., by ICD 14 or pacemaker 100, may cause interference with the sensing circuitry of the transmitting IMD, resulting in false sensing of a cardiac event. Such false sensing of cardiac events due to TCC interference with a cardiac event detector included in electrical signal sensing circuitry may lead to withholding of a pacing pulse when a pacing pulse is actually needed or contribute to false detection of a tachyarrhythmia event. The TCC signal transmission techniques disclosed herein reduce the likelihood of a TCC signal being falsely detected as a cardiac event by a cardiac electrical signal sensing circuit of the transmitting device.

The TCC signal transmission techniques may also reduce the likelihood that another IMD implanted in patient 12 that is configured to sense electrophysiological signals, such as R-waves and/or P-waves, falsely senses TCC signals as physiological signals. Another IMD implanted in patient 12 may be the intended receiving device of the transmitted TCC signals, e.g., pacemaker 100 receiving signals from ICD 14 or vice versa. In other cases, another IMD co-implanted in patient 12 may not be the intended receiving device of transmitted TCC signals but may be configured to sense electrophysiological signals via electrodes coupled to the co-implanted IMD. A voltage signal may develop across sensing electrodes of the intended or unintended receiving device and interfere with electrophysiological sensing and event detection. The TCC signal transmission techniques of the present disclosure may reduce or eliminate the incidence of TCC signals being sensed as electrophysiological signals or events by any other IMD implanted in patient 12 or an external device having electrodes coupled to the patient externally.

FIG. 1 is described in the context of IMD system 10 including ICD 14 and pacemaker 100 capable of sensing cardiac electrical signals produced by the patient's heart 8 and delivering cardioversion and/or defibrillation (CV/DF) shocks and cardiac pacing pulses to the patient's heart 8. In some examples, the TCC communication may be "one-way" communication, e.g., transmission only from ICD 14 to pacemaker 100 or transmission only from pacemaker 100 to ICD 14. In other examples, the TCC communication may be "two-way" communication between ICD 14 and pacemaker 100 such that each of pacemaker 100 and ICD 14 can receive and transmit information. It is recognized that aspects of the TCC signal transmission techniques disclosed herein may be implemented in a variety of IMD systems which may include an ICD, pacemaker, cardiac monitor or other sensing-only device, neurostimulator, drug delivery device or other implantable medical device(s). The TCC signal transmission techniques disclosed herein may be implemented in any IMD system that requires communication between one IMD and at least one other medical device, implanted or external. Moreover, the techniques described herein may be utilized by two external devices that communicate using TCC. The techniques may also have non-medical applications as well for devices that are implanted and/or external and communicate using TCC.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). In other instances, the housing 15 of ICD 14 may include a plurality of electrodes on an outer portion of the housing. The outer portion(s) of the housing 15 functioning as an electrode(s) may be coated with a material, such as titanium nitride for reducing post-stimulation polarization artifact. Housing 15 may be used as an active can electrode for use in delivering CV/DF shocks or other high voltage pulses delivered using a high voltage therapy circuit. In other examples, housing 15 may be available for use in delivering relatively lower voltage cardiac pacing pulses and/or for sensing cardiac electrical signals in combination with electrodes carried by lead 16. In any of these examples, housing 15 may be used in a transmitting electrode vector for transmitting TCC signals according to the techniques disclosed herein.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, TCC transmitting and receiving circuitry, power sources and other components for sensing cardiac electrical signals, detecting a heart rhythm, and controlling and delivering electrical stimulation pulses to treat an abnormal heart rhythm and for transmitting TCC signals to pacemaker 100 and/or receiving TCC signals from pacemaker 100.

Lead 16 includes an elongated lead body 18 having a proximal end 27 that includes a lead connector (not shown) configured to be connected to ICD connector assembly 17 and a distal portion 25 that includes one or more electrodes.

In the example illustrated in FIG. 1, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be selectively activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality, and/or TCC signal transmission and receiving in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a sensing vector used to sense cardiac electrical signals and detect and discriminate tachyarrhythmias. Electrodes 24 and 26 may be used in a TCC signal transmitting electrode vector in combination with each other, collectively with housing 15, or individually with housing 15. In the case of ICD 14 being configured to receive TCC signals from pacemaker 100, electrodes 24, 26 and/or housing 15 may be used in a TCC receiving electrode vector. The transmitting and receiving electrode vectors may be the same or different vectors.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., delivery of relatively low voltage pacing pulses and/or sensing of cardiac electrical signals, as opposed to delivering high voltage CV/DF shocks. In some instances, electrodes 28 and 30 may provide only pacing functionality, only sensing functionality or both. Furthermore, one or both of electrodes 28 and 30 may be used in TCC signal transmitting and/or receiving electrode vectors in some examples.

ICD 14 may obtain cardiac electrical signals corresponding to electrical activity of heart 8 via a combination of sensing electrode vectors that include combinations of electrodes 24, 26, 28, 30 and/or housing 15. Various sensing electrode vectors utilizing combinations of electrodes 24, 26, 28, and 30 may be selected by sensing circuitry included in ICD 14 for receiving a cardiac electrical signal via one or more sensing electrode vectors.

In the example illustrated in FIG. 1, electrode 28 is located proximal to defibrillation electrode 24, and electrode 30 is located between defibrillation electrodes 24 and 26. Electrodes 28 and 30 may be ring electrodes, short coil electrodes, hemispherical electrodes, or the like. Electrodes 28 and 30 may be positioned at other locations along lead body 18 and are not limited to the positions shown. In other examples, lead 16 may include none, one or more pace/sense electrodes and/or one or more defibrillation electrodes.

A TCC transmitting electrode vector may be selected from defibrillation electrodes 24, 26, 28, 30 and housing 15 for transmitting TCC signals produced by a TCC transmitter included in ICD 14. Electrodes, such as defibrillation electrodes 24 and 26 and housing 15, having a relatively large surface area may be used to transmit TCC signals to minimize the impedance of the transmitting electrode vector. A low impedance of the transmitting electrode vector maximizes the injected current signal.

The TCC transmitting electrode vector may be selected to both minimize impedance of the transmitting electrode pair and maximize transimpedance from the transmitting electrode pair to the intended receiving electrode pair. As used herein, the term "transimpedance" refers to the voltage received at a TCC signal receiving electrode pair divided by the transmitted current (voltage out divided by current in). As such, the transimpedance for a given TCC communication electrode vector for each of two IMDs configured to communicate bidirectionally is the same for communication in both directions for a given set of transmitting and receiving electrode vectors. By maximizing transimpedance, the voltage signal at the intended receiving electrodes is maximized for a given current signal injected into the tissue conductance pathway. As such, a low impedance of the transmitting electrode vector and high transimpedance of the TCC pathway increases the received TCC signal strength (voltage signal) at the receiving electrode vector.

Among the factors that may contribute to a maximized transimpedance of the TCC pathway are a substantially parallel electrical configuration of the transmitting and receiving electrode vectors, relatively wide spacing of the transmitting electrodes, relatively wide spacing of the receiving electrodes, and close proximity of the transmitting electrode vector to the receiving electrode vector. A transmitting electrode vector closer in proximity to the receiving electrode vector improves the strength of the TCC signal compared to a larger separation between the transmitting electrode vector and the receiving electrode vectors. The optimal orientation for the receiving electrode vector is parallel to the conductive tissue pathway of the injected current flow. A transmitting electrode vector that is substantially electrically parallel to the receiving electrode vector improves the strength of the TCC signal compared to the receiving electrode vector being orthogonal to the pathway of the current flow through the body tissue, which may result in a null signal.

A parallel electrical configuration between the transmitting and receiving electrode vectors may coincide with physically parallel electrode vectors. The physical electrode vectors may be viewed in some cases as the line the extends from one electrode of the vector to the other electrode of the vector to determine orientation of the transmitting and received vectors relative to one another. In some instances, however, physically parallel electrode vectors may not be electrically parallel depending on the electrical conduction properties of the intervening tissues. For example, a body tissue having relatively low electrical conductance, such as lung tissue, compared to other surrounding tissues, may require a physical electrode configuration that is not necessarily parallel in order to achieve an electrical configuration that is substantially parallel.

The TCC transmitting electrode vector may be selected to include electrodes that are not coupled to ICD sensing circuitry, e.g., a cardiac event detector configured to sense R-waves and/or P-waves from an electrical signal received by a sensing electrode vector. Use of an electrode for TCC signal transmission that is also coupled to a cardiac electrical event detector or other electrical signal sensing circuitry may increase interference with cardiac event detection or other electrical signal monitoring. The transmitting electrode vector may be selected to include at least one or both electrodes that are not coupled to the cardiac electrical event detector of ICD 14 so that TCC signals that are unintentionally received by the cardiac event detector are received via a transimpedance pathway from the transmitting electrode vector to the sensing electrode vector rather than directly through the sensing electrode impedance.

In other examples, however, the TCC transmitting electrode vector may include one or more electrodes coupled to a cardiac electrical event detector included in ICD 14. A transmitting electrode vector may include electrodes coupled to ICD sensing circuitry when the resulting transmitting electrode vector is optimal in other ways, e.g., low impedance and high transimpedance. Transmission of TCC signals using one or both electrodes included in a sensing electrode vector coupled to a cardiac event detector may be selected in a trade-off for optimizing other considerations in achieving reliable TCC signal transmission and reception. TCC signal transmission techniques disclosed herein may reduce or eliminate interference of the TCC signal transmission with cardiac signal sensing and cardiac electrical event detection (or other electrophysiological signal sensing) as well as other sensing functions such as electrical impedance monitoring of a medical electrical lead or body tissue.

In one example, defibrillation electrode 24 may be selected in combination with housing 15 for transmitting TCC signals to pacemaker 100. In other examples, TCC signals may be transmitted by ICD 14 using defibrillation electrode 26 and housing 15 or using the two defibrillation electrodes 24 and 26. The transmitting electrode vector impedance (delivered voltage divided by delivered current) may be up to hundreds of ohms. The transimpedance of the TCC pathway that includes a transmitting electrode vector including one defibrillation electrode 24 or 26 paired with housing 15 may be less than 10 ohms and even less than 1 ohm. A high transimpedance at the TCC signal transmission frequency is desired to produce a relatively high voltage on the receiving electrodes for a given injected current of the TCC signal.

The electrode vector selected for transmitting TCC signals may include one or both of pace/sense electrodes 28 and 30 in some examples. For example, the pace/sense electrode 28 or 30 may be paired with housing 15, defibrillation electrode 24 or defibrillation electrode 26 for transmitting TCC signals. The impedance of the transmitting electrode vector may be increased due to the relatively smaller surface area of pace/sense electrodes 28 and 30, which may have the effect of lowering the injected current during TCC signal transmission and thereby lowering the received voltage signal at the receiving electrode vector.

ICD 14 may be configured to select a TCC transmitting electrode vector from among multiple possible vectors using electrodes 24, 26, 28, 30 and housing 15 to achieve the best TCC signal strength at the receiving electrodes of pacemaker 100 and/or minimize TCC signal interference with cardiac event detection, impedance monitoring, or other functions performed by the ICD sensing circuit and/or by a sensing circuit of pacemaker 100. In some examples, multiple vectors may be used to transmit TCC signals to cover different angles in three-dimensional space to achieve at least one TCC transmitting electrode vector that is substantially electrically parallel to the receiving electrode vector. The electrical configuration of a single transmitting electrode vector relative to the TCC receiving electrode vector may be time varying due to heart motion when the receiving electrode vector is within or coupled to the patient's heart, as in the case of pacemaker 100.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum or substernally under the ribcage and/or sternum 22. Although illustrated in FIG. 1 as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous, submuscular or substernal paths. The path of extra-cardiovascular lead 16 may depend on the location of ICD 14, the arrangement and position of electrodes carried by the lead body 18, and/or other factors.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry of ICD 14, such as a signal generator for therapy delivery and TCC signal transmission and/or a sensing circuit for sensing cardiac electrical signals and/or receiving TCC signals, via connections in the connector assembly 17, including associated electrical feedthroughs crossing housing 15.

The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14. The electrical conductors also transmit TCC signals from a TCC transmitter to electrodes selected for transmitting the TCC signals. In some examples, ICD 14 may receive TCC signals from pacemaker 100 in which case the TCC signals are conducted from a receiving pair of electrodes of ICD 14 to a TCC signal receiver enclosed by housing 15.

The lead body 18 of lead 16 may be formed from a non-conductive material and shaped to form one or more lumens within which the one or more conductors extend. Lead body 18 may be a flexible lead body that conforms to an implant pathway. In other examples, lead body 18 may include one or more preformed curves. Various example configurations of extra-cardiovascular leads and electrodes and dimensions that may be implemented in conjunction with the TCC transmission techniques disclosed herein are described in pending U.S. Publication No. 2015/0306375 (Marshall, et al.) and pending U.S. Publication No. 2015/0306410 (Marshall, et al.), both of which are incorporated herein by reference in their entirety.

ICD 14 analyzes the cardiac electrical signals received from one or more sensing electrode vectors to monitor for abnormal rhythms, such as bradycardia, tachycardia or fibrillation. ICD 14 may analyze the heart rate and morphology of the cardiac electrical signals to monitor for tachyarrhythmia in accordance with any of a number of tachyarrhythmia detection techniques. ICD 14 generates and delivers electrical stimulation therapy in response to detecting a tachyarrhythmia, e.g., ventricular tachycardia (VT) or ventricular fibrillation (VF), using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

Pacemaker 100 is shown as a leadless intracardiac pacemaker configured to receive TCC signals from ICD 14 via housing-based electrodes in the examples presented herein and may be configured to transmit TCC signals via housing-based electrodes to ICD 14. Pacemaker 100 may be delivered transvenously and anchored by a fixation member at an intracardiac pacing and sensing site. For example, pacemaker 100 may be implanted in an atrial or ventricular chamber of the patient's heart. In further examples, pacemaker 100 may be attached to an external surface of heart 8 (e.g., in contact with the epicardium) such that pacemaker 100 is disposed outside of heart 8.

Pacemaker 100 is configured to deliver cardiac pacing pulses via a pair of housing-based electrodes and may be configured to sense cardiac electrical signals for determining the need and timing of a delivered pacing pulse. For example, pacemaker 100 may deliver bradycardia pacing pulses, rate responsive pacing pulses, ATP, post-shock pacing pulses, CRT, and/or other pacing therapies. Pacemaker 100 may include a TCC receiver that receives and demodulates TCC signals transmitted from ICD 14. Pacemaker 100 may include a TCC transmitter that transmits TCC signals to ICD 14. Pacemaker 100 is described in greater detail below in conjunction with FIG. 3. An example intracardiac pacemaker that may be included in an IMD system employing TCC is described in U.S. Pat. No. 8,744,572 (Greenhut et al.) incorporated herein by reference in its entirety.

In some examples, pacemaker 100 may be implanted in the right atrium, the right ventricle or the left ventricle of heart 8 to sense electrical activity of heart 8 and deliver pacing therapy. In other examples, system 10 may include two or more intracardiac pacemakers 100 within different chambers of heart 8 (e.g., within the right atrium, the right ventricle, and/or left ventricle). ICD 14 may be configured to transmit TCC signals to one or more pacemakers implanted within the patient's heart 8 to coordinate electrical stimulation therapy delivery. For example, ICD 14 may transmit command signals to cause pacemaker 100 to deliver a cardiac pacing pulse, ATP therapy, or request confirmation of sensed cardiac electrical events or a tachyarrhythmia detection.

An external device 40 is shown in telemetric communication with ICD 14 by a wireless communication link 42 and pacemaker 100 via a wireless communication link 44. External device 40 may include a processor, display, user interface, telemetry unit and other components for communicating with ICD 14 and pacemaker 100 for transmitting and receiving data via communication link 42 and 44, respectively. Communication link 42 or 44 may be established between ICD 14 or pacemaker 14, respectively, and external device 40 using a radio frequency (RF) link such as BLUETOOTH®, Wi-Fi, or Medical Implant Communication Service (MICS) or other RF or communication frequency bandwidth. In some examples, ICD 14 and/or pacemaker 100 may communicate with an external device 40 using TCC, e.g., using surface electrodes placed externally on patient 12 and coupled to external device 40.

External device 40 may be embodied as a programmer used in a hospital, clinic or physician's office to retrieve data from ICD 14 and to program operating parameters and algorithms in ICD 14 for controlling ICD functions. External device 40 may be used to program cardiac event sensing parameters (e.g., R-wave sensing parameters), cardiac rhythm detection parameters (e.g., VT and VF detection parameters) and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand-held device, such as a smart phone, tablet or other hand-held device.

In some examples, pacemaker 100 is not capable of bidirectional communication with external device 40. ICD 14 may operate as a control device and pacemaker 100 as a responder. Pacemaker 100 may receive TCC communication signals from ICD 14 that include operating control data and commands (which may be transmitted from external device 40 to ICD 14) so that RF telemetry circuitry need not be included in pacemaker 100. Pacemaker 100 may transmit data, such as information related to delivered pacing therapy and/or acquired cardiac electrical signals to ICD 14 via TCC transmissions, and ICD 14 may transmit data received from pacemaker 100 to external device 40 via RF communication. Alternatively, pacemaker 100 may periodically transmit data to ICD 14, which stores it until receiving a request from external device 40.

Figure 2:
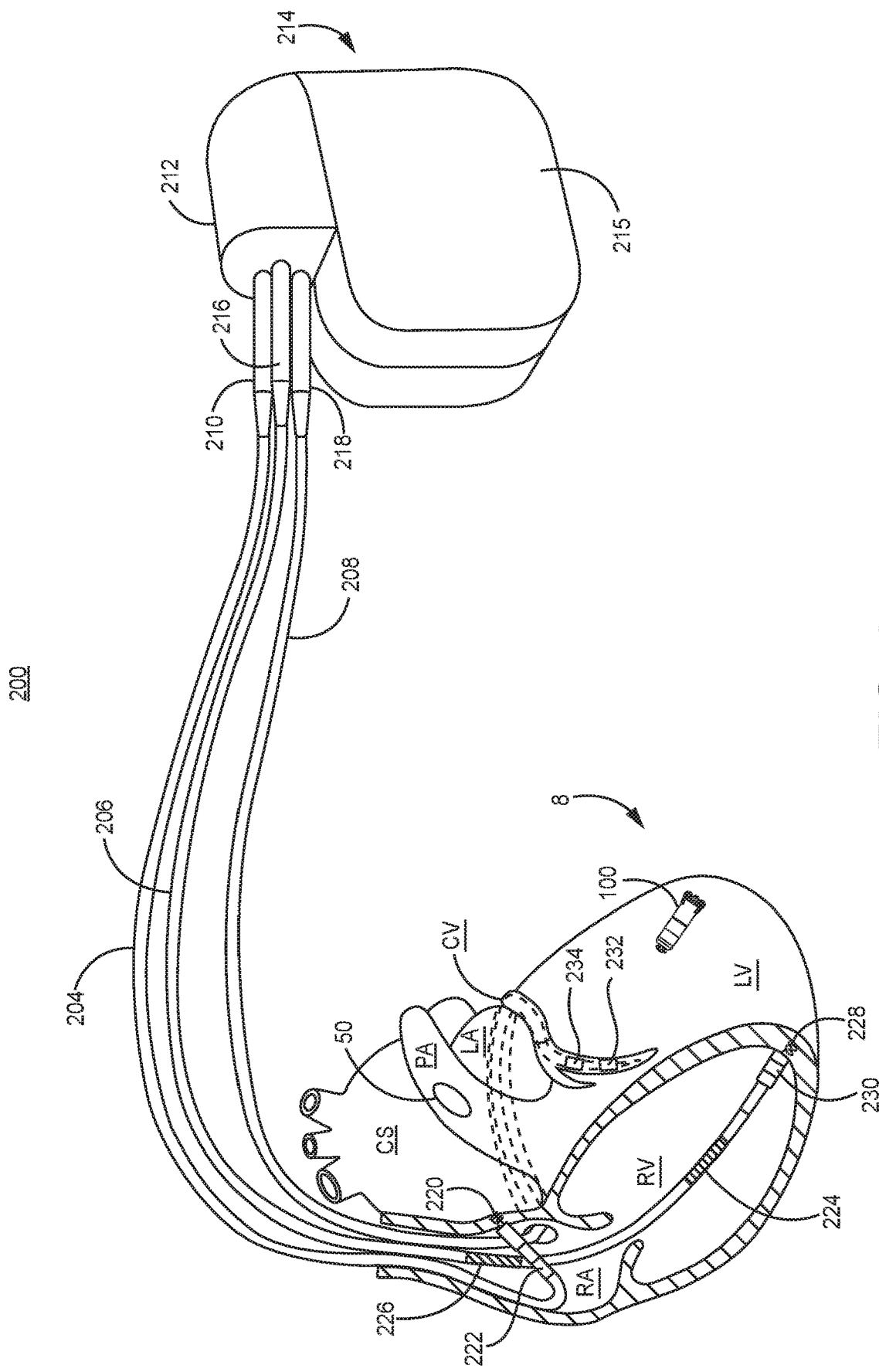
FIG. 2 is a conceptual diagram of an IMD system configured to communicate using TCC techniques disclosed herein according to another example.

FIG. 2 is a conceptual diagram of an IMD system 200 configured to communicate using TCC transmission techniques disclosed herein according to another example. The IMD system 200 of FIG. 2 includes an ICD 214 coupled to a patient's heart 8 via transvenous electrical leads 204, 206, and 208. IMD system 200 may include a leadless pacemaker 100 and/or a leadless sensor 50. Sensor 50 is shown as a leadless pressure sensor positioned in the pulmonary artery for monitoring pulmonary arterial pressure. Leadless pressure sensor 50, also referred to herein as "pressure sensor" 50, may be positioned at other intracardiac or arterial locations for monitoring blood pressure. In other examples, the IMD system 200 (or IMD system 10 of FIG. 1) may include other wireless sensors performing sensing-only or monitoring-only functions configured to send and/or receive TCC signals to/from ICD 214 (or ICD 14 of FIG. 1) and/or pacemaker 100. Other wireless sensors may include, for example, an electrogram (EGM) monitor, an electrocardiogram (ECG) monitor, an oxygen monitor, acoustical monitor, accelerometer, bioimpedance monitor, pH monitor, temperature monitor, insulin monitor, or other sensing device including one or any combination of sensors.

ICD 214 includes a connector block 212 that may be configured to receive the proximal ends of a right atrial (RA) lead 204, a right ventricular (RV) lead 206 and a coronary sinus (CS) lead 208, which are advanced transvenously for positioning electrodes for sensing and stimulation in three or all four heart chambers. RV lead 206 is positioned such that its distal end is in the right ventricle for sensing RV cardiac signals and delivering pacing or shocking pulses in the right ventricle. For these purposes, RV lead 206 is equipped with pacing and sensing electrodes shown as a tip electrode 228 and a ring electrode 230. RV lead 206 is further shown to carry defibrillation electrodes 224 and 226, which may be elongated coil electrodes used to deliver high voltage CV/DF pulses. Defibrillation electrode 224 may be referred to herein as the "RV defibrillation electrode" or "RV coil electrode" because it may be carried along RV lead 206 such that it is positioned substantially within the right ventricle when distal pacing and sensing electrodes 228 and 230 are positioned for pacing and sensing in the right ventricle. Defibrillation electrode 226 may be referred to herein as a "superior vena cava (SVC) defibrillation electrode" or "SVC coil electrode" because it may be carried along RV lead 206 such that it is positioned at least partially along the SVC when the distal end of RV lead 206 is advanced within the right ventricle.

Each of electrodes 224, 226, 228 and 230 are connected to a respective insulated conductor extending within the body of RV lead 206. The proximal end of the insulated conductors are coupled to corresponding connectors carried by proximal lead connector 216, e.g., a DF-4 connector, for providing electrical connection to ICD 214. It is understood that although ICD 214 is illustrated in FIG. 2 as a multi-chamber device coupled to RA lead 204 and CS lead 208 in addition to RV lead 206, ICD 214 may be configured as a dual-chamber device coupled to only two transvenous leads or a single-chamber device coupled to only one transvenous lead. For example, ICD 214 may be a single chamber device coupled only to RV lead 206 and may be configured to perform the TCC techniques disclosed herein using the available electrodes 224, 226, 228, and 230 and/or housing 215 in addition to receiving cardiac electrical signals from heart 8 and delivering electrical stimulation therapy to heart 8.

RA lead 204 is positioned such that its distal end is in the vicinity of the right atrium and the superior vena cava. Lead 204 is equipped with pacing and sensing electrodes 220 and 222, shown as a tip electrode 220 and a ring electrode 222 spaced proximally from tip electrode 220. The electrodes 220 and 222 provide sensing and pacing in the right atrium and are each connected to a respective insulated conductor within the body of RA lead 206. Each insulated conductor is coupled at its proximal end to a connector carried by proximal lead connector 210.

CS lead 208 is advanced within the vasculature of the left side of the heart via the coronary sinus (CS) and a cardiac vein (CV). CS lead 208 is shown in FIG. 2 as having one or more electrodes 232, 234 that may be used in delivering pacing and/or sensing cardiac electrical signals in the left chambers of the heart, i.e., the left ventricle and/or the left atrium. The one or more electrodes 232, 234 of CS lead 208 are coupled to respective insulated conductors within the body of CS lead 208, which provide connection to the proximal lead connector 218.

Any of electrodes 220, 222, 224, 226, 228, 230, 232, 234 may be selected by ICD 214 in a TCC electrode vector for transmitting and/or receiving TCC signals. In some examples, housing 215 is selected in a TCC transmitting electrode vector along with a lead-based defibrillation electrode, e.g., RV coil electrode 224 or SVC coil electrode 226, to provide a low impedance and high transimpedance TCC transmitting electrode vector. In other examples, TCC transmission is performed using the RV coil electrode 224 and the SVC coil electrode 226. In still other examples, an electrode 232 or 234 carried by the CS lead 208 may be selected in combination with housing 215, RV coil electrode 224, or SVC coil electrode 226. It is recognized that numerous TCC transmitting electrode vectors may be available using the various available electrodes carried by one or more of leads 204, 206 and 208 coupled to ICD 214. In some examples, multiple transmitting electrode vectors may be selected to promote transmission via a vector that is substantially parallel (electrically) to the housing-based electrodes of pacemaker 100 or to receiving electrodes of leadless pressure sensor 50 for transmitting signals to the respective pacemaker 100 or pressure sensor 50.

Housing 215 encloses internal circuitry generally corresponding to the various circuits and components described in conjunction with FIG. 5 below, for sensing cardiac signals from heart 8, detecting arrhythmias, controlling therapy delivery and performing TCC with pacemaker 100 and/or pressure sensor 50 using the techniques disclosed herein. It is recognized that these TCC transmission techniques may be practiced in conjunction with alternative lead and electrode configurations other than those depicted in the examples of FIG. 1 and FIG. 2.

Pressure sensor 50 may be implanted in the pulmonary artery of the patient for monitoring the pulmonary arterial pressure as an indication of the hemodynamic status of the patient 12. One example of pressure sensor 50 is described below in conjunction with FIG. 4. Pressure sensor 50 may be configured to receive pressure signals via a pressure sensor and receive TCC signals by a TCC receiver via electrodes carried by the housing of the pressure sensor 50.

In the examples of FIGS. 1 and 2, two or more IMDs may be co-implanted in patient 12 and communicate via TCC to enable a system level of functionality such as sharing the detection of arrhythmias between devices, synchronized timing of CV/DF shocks, ATP, and/or post-shock pacing, optimization of the resources (e.g., battery capacity or processing power) available to each device, or sharing or coordination of physiological signal acquisition. In some examples, communication between the ICD 14 or ICD 214 and pacemaker 100 may be used to initiate therapy and/or confirm that therapy should be delivered. Communication between ICD 14 or ICD 214 and pressure sensor 50 may be used to initiate pressure signal acquisition and/or retrieval of pressure signal data from pressure sensor 50. One approach is for ICD 14 or ICD 214 to function as a control device and pacemaker 100 and/or sensor 50 to function as responders. For instance, a TCC signal from ICD 14 or ICD 214 may cause pacemaker 100 to deliver a cardiac pacing pulse or therapy.

In another example, ICD 214 may transmit a TCC command signal to pressure sensor 50 for causing pressure sensor 50 to begin acquiring a pressure signal. Pressure sensor 50 may be configured to transmit pressure signal data via TCC to ICD 214 or to external device 40 (shown in FIG. 1). ICD 214 may transmit a TCC command to pressure sensor 50 to cause pressure sensor 50 to transmit a pressure signal in real time, transmit a pressure signal previously acquired and stored by pressure sensor 50, or transmit pressure data derived from a pressure signal received by pressure sensor 50. In other examples, pressure sensor 50 may be configured to transmit pressure signal data via RF telemetry to ICD 214 and/or to an external device, such as device 40 shown in FIG. 1 in response to a TCC command signal received from ICD 214.

During TCC signal transmission, current is driven through the patient's body tissue between two or more electrodes of the transmitting IMD (e.g., ICD 14 or ICD 214). The current spreads through the patient's body, e.g., through the thorax, producing a potential field. The receiving IMD (e.g., pacemaker 100 or pressure sensor 50 or other implanted or external device) may detect the TCC signal by measuring the potential difference between two of its electrodes, e.g., two housing-based electrodes of pacemaker 100 or sensor 50. Optimally, the receiving electrodes are parallel to the tissue conduction pathway of the injected current to maximize the potential difference developed on the receiving electrode vector. The current injected to transmit the TCC signal is of sufficient amplitude to produce a voltage potential that can be detected by an intended receiving IMD but should at the same time not capture excitable body tissue, e.g., causing unintended stimulation of nerve or muscle tissue, possibly leading to muscle contraction, pain or even cardiac capture. Any unintended stimulation of nerve or muscle tissue also likely increases noise received on the sensing electrodes of a device of system 10 or 200.

In some cases, a co-implanted IMD may be an unintended receiver of the TCC signal. If a co-implanted IMD includes electrodes or is coupled to electrodes for receiving electrical signals, but is not the intended receiver of a TCC signal, a voltage potential may develop across the electrodes of the unintended receiver leading to interference with the normal signal detection function of the unintended receiver. For example, in system 200, ICD 214 and pressure sensor 50 may be configured to communicate using TCC. Pacemaker 100 may be co-implanted with ICD 214 and pressure sensor 50 but not configured to send or receive TCC signals. A TCC signal transmitted by ICD 214 to pressure sensor 50 may result in voltage developed across the housing-based electrodes of pacemaker 100. Pacemaker 100 may be an unintended receiver of the transmitted TCC signal. The voltage developed across the housing-based electrodes of pacemaker 100 may interfere with a cardiac event detector included in pacemaker 100. In other examples, a subcutaneous cardiac electrical signal monitor having housing-based electrodes for monitoring a subcutaneously-acquired electrocardiogram (ECG) signal, such as the REVEAL LINQ™ Insertable Cardiac Monitor (available from Medtronic, Inc., Minneapolis, Minn., USA) may be implanted in a patient having two other IMDs configured to communicate via TCC, such as ICD 214 and pressure sensor 50. The cardiac electrical signal monitor may be an unintended receiver of TCC signals transmitted between ICD 214 and pressure sensor 50. The methods disclosed herein for transmitting TCC signals may eliminate or minimize interference of TCC signals with electrical signal sensing circuitry of other IMDs or external devices in or on the patient, which may be intended or unintended receivers.

While particular IMD systems 10 and 200, including an ICD 14 or ICD 214, respectively, pacemaker 100 and/or pressure sensor 50 are shown in the illustrative examples of FIGS. 1 and 2, methodologies described herein for TCC transmission may be used with other IMD systems including other types and locations of IMDs as well as other lead and electrode arrangements. For example, an implantable cardiac monitor, such as the REVEAL LINQ™ Insertable Cardiac Monitor, may be utilized as a relay device for leadless pacemaker 100 and/or pressure sensor 50 by receiving data from those devices via TCC and transmitting that data to an external device 40 via RF communication, such as BLUETOOTH™ communication. Generally, this disclosure describes various techniques for transmitting TCC signals by an IMD that includes sensing circuitry for sensing a cardiac electrical signal. The TCC signal transmission techniques reduce the likelihood that a TCC signal is oversensed as a physiological event by the sensing circuitry of the transmitting device. The TCC transmission techniques may also reduce the likelihood of TCC signal oversensing by sensing circuitry included in another IMD co-implanted with the transmitting device or an external device having electrodes coupled to the patient. Another IMD co-implanted with the transmitting device (or the external device) may be the intended receiving device of the TCC signal transmission or another medical device that is not the targeted recipient and may not even be configured to receive and detect TCC communication signals.

Figure 3A:
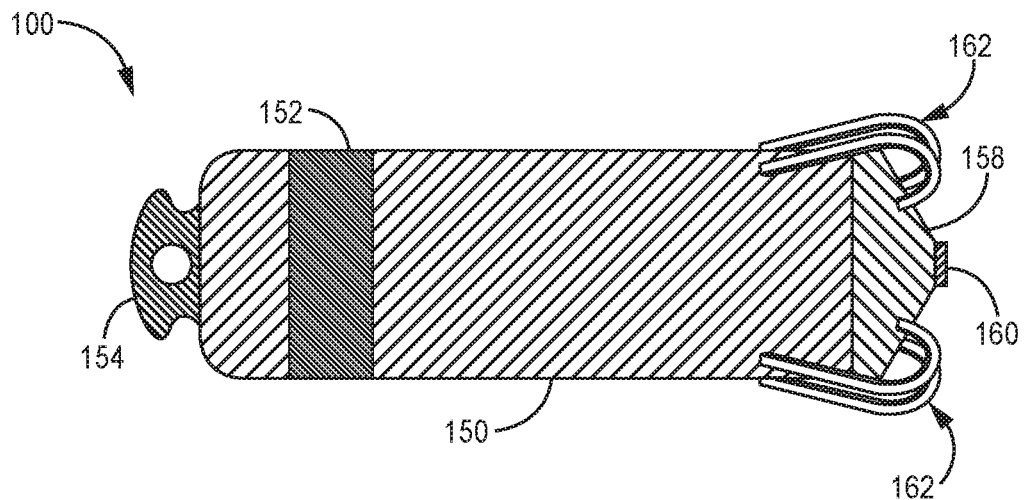
FIG. 3A is a conceptual diagram of a leadless intracardiac pacemaker according to one example.

FIG. 3A is a conceptual diagram of pacemaker 100 according to one example. As shown in FIG. 3A, pacemaker 100 may be a leadless pacemaker including a housing 150, housing end cap 158, distal electrode 160, proximal electrode 152, fixation member 162, and a delivery tool interface member 154. Housing 150, sealed with end cap 158, encloses and protects the various electrical components within pacemaker 100. Pacemaker 100 is shown including two electrodes 152 and 160 but may include two or more electrodes for delivering cardiac electrical stimulation pulses (such as pacing pulses or ATP), sensing cardiac electrical signals for detecting cardiac electrical events, and for receiving and/or transmitting TCC signals.

Electrodes 152 and 160 are carried on the housing 150 and housing end cap 158. In this manner, electrodes 152 and 160 may be considered housing-based electrodes. In other examples, one or more electrodes may be coupled to circuitry enclosed by housing 150 via an electrode extension extending away from housing 150. In the example of FIG. 3A, electrode 160 is disposed on the exterior surface of end cap 158. Electrode 160 may be a tip electrode positioned to contact cardiac tissue upon implantation and fixation at a pacing site by fixation member 162. Electrode 152 may be a ring or cylindrical electrode disposed along the exterior surface of housing 150. Both housing 150 and housing end cap 158 may be electrically insulating. In some examples, housing 150 is an electrically conductive material, e.g., a titanium alloy or other biocompatible metal or metal alloy. Portions of housing 150 may be coated with a non-conductive material, e.g., parylene, polyurethane, silicone or other biocompatible polymer, to insulate portions of housing 150 not functioning as electrode 152.

Electrodes 160 and 152 may be used as a cathode and anode pair for cardiac pacing therapy and receiving and/or transmitting TCC signals. In addition, electrodes 152 and 160 may be used to detect intrinsic electrical signals from the patient's heart 8. In other examples, pacemaker 100 may include three or more electrodes, where any two or more of the electrodes may be selected to form a vector for delivery of electrical stimulation therapy, detecting intrinsic cardiac electrical signals from the patient's heart 8, transmitting TCC signals, and receiving TCC signals. In some examples in which pacemaker 100 includes three or more electrodes, two or more of the electrodes may be selected, e.g., via switches, to form a vector for TCC. Pacemaker 100 may use multiple vectors for TCC transmission or receiving, for example, to promote a substantially parallel electrical configuration with a TCC transmitting electrode vector of ICD 14 or ICD 214, which may increase the transimpedance and increase the received voltage signal.

Fixation member 162 may include multiple tines of a shape memory material that retains a preformed curved shape as shown. During implantation, fixation member 162 may be flexed forward to pierce tissue and elastically flex back towards housing 150 to regain the pre-formed curved shape. In this manner, fixation member 162 may be embedded within cardiac tissue at the implant site. In other examples, fixation member 162 may include helical fixation tines, barbs, hooks or other fixation features.

Delivery tool interface member 154 may be provided for engaging with a delivery tool used to advance pacemaker 100 to an implant site. A delivery tool may be removably coupled to delivery tool interface member 154 for retrieving pacemaker 100 back into a delivery tool if removal or repositioning of pacemaker 100 is required.

Figure 3B:
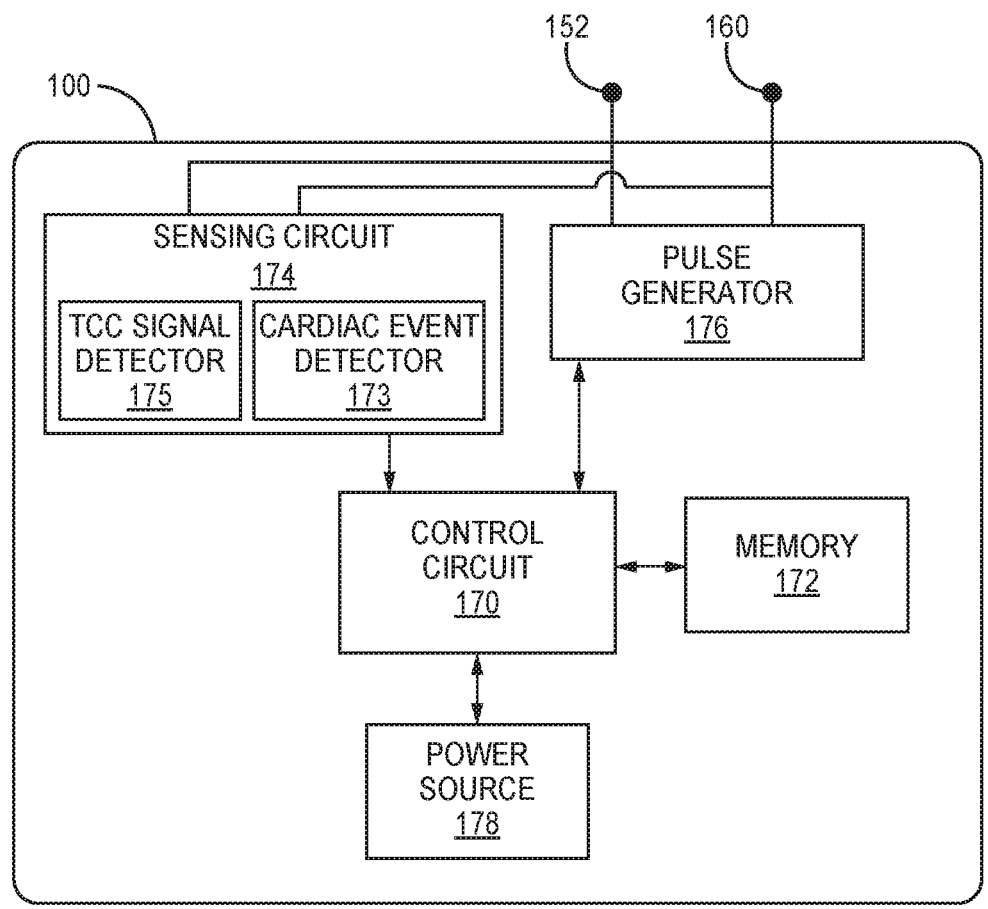
FIG. 3B is a schematic diagram of circuitry that may be included in the pacemaker of FIG. 3A according to one example.

FIG. 3B is a schematic diagram of circuitry that may be enclosed by pacemaker housing 150 according to one example. Pacemaker housing 150 may enclose a control circuit 170, memory 172, pulse generator 176, sensing circuit 174, and a power source 178. Control circuit 170 may include a microprocessor and/or other control circuitry for controlling the functions attributed to pacemaker 100 herein, such as controlling pulse generator 176 to deliver signals via electrodes 152 and 160 and controlling sensing circuit 174 to detect signals from electrical signals received via electrodes 152 and 160. Power source 178 may include one or more rechargeable or non-rechargeable batteries for providing power to control circuit 170, memory 172, pulse generator 176 and sensing circuit 174 as needed. Control circuit 170 may execute instructions stored in memory 172 and may control pulse generator 176 and sensing circuit 174 according to control parameters stored in memory 172, such as various timing intervals, pacing pulse parameters and cardiac event sensing parameters.

Pulse generator 176 generates therapeutic pacing pulses delivered via electrodes 152 and 160 under the control of timing circuitry included in control circuit 170. Pulse generator 176 may include charging circuitry, one or more charge storage devices such as one or more capacitors, and switching circuitry that couples the charge storage device(s) to an output capacitor coupled to electrodes 160 and 152 to discharge the charge storage devices via electrodes 160 and 152. In some examples, pulse generator includes a TCC transmitter (standalone or as part of a transceiver), such as the transmitter described below in conjunction with FIG. 6, for generating TCC signals transmitted via electrodes 160 and 152. Power source 178 provides power to the charging circuit of pulse generator 176 and the TCC transmitter when present.

Pacemaker 100 may be configured for sensing cardiac electrical signals, e.g., R-waves or P-waves, and include a cardiac event detector 173. Intrinsic cardiac electrical events may be detected from an electrical signal produced by the heart and received via electrodes 152 and 160. Cardiac event detector 173 may include filters, amplifiers, an analog-to-digital converter, rectifier, comparator, sense amplifier or other circuitry for detecting cardiac events from a cardiac electrical signal received via electrodes 152 and 160. Under the control of control circuit 170, cardiac event detector 173 may apply various blanking and/or refractory periods to circuitry included in event detector 173 and an auto-adjusting cardiac event detection threshold amplitude, e.g., an R-wave detection threshold amplitude or a P-wave detection threshold amplitude, to the electrical signal received via electrodes 152 and 160.

Sensing circuit 174 may further include a TCC signal detector 175 for detecting a TCC signal from ICD 14 (or ICD 214). A voltage potential develops across electrodes 152 and 160 in response to current conducted via a tissue pathway during TCC signal transmission from ICD 14 or 214. The voltage signal may be received and demodulated by TCC signal detector 175 and decoded by control circuit 170. TCC signal detector 175 may include amplifiers, filters, analog-to-digital converters, rectifiers, comparators, counters, a phase locked loop and/or other circuitry configured to detect a wakeup beacon signal from a transmitting device and detect and demodulate the modulated carrier signal transmitted in data packets including encoded data. For example, TCC signal detector 175 of pacemaker 100 (and other TCC signal detectors referred to herein) may include a pre-amplifier and a high-Q filter tuned to the carrier frequency of a carrier signal that is used to transmit beacon signals and data signals during a TCC transmission session. The filter may be followed by another amplifier and a demodulator that converts the received signals to a binary signal representing coded data.

The circuitry of TCC signal detector 175 may include circuitry shared with cardiac event detector 173 in some examples. The filters included in TCC signal detector 175 and cardiac event detector 173, however, are expected to operate at different passbands, for example, for detecting different signal frequencies. The TCC signals may be transmitted with a carrier frequency in the range of 33 to 250 kHz, in the range of 60 to 200 kHz, or at 100 kHz as examples. Cardiac electrical signals generated by heart 8 are generally less than 100 Hz. The TCC signal transmission techniques disclosed herein may reduce or eliminate oversensing of a received TCC signal, e.g., transmitted from ICD 14 or ICD 214, as a cardiac electrical event by cardiac event detector 173. In examples that include a TCC transmitter in pacemaker 100, the TCC signal transmission techniques disclosed herein may reduce or prevent oversensing of a TCC signal produced by the TCC transmitter and transmitted via electrodes 152 and 160 from being detected as a cardiac event by cardiac event detector 173. In some instances, the TCC transmitter may include circuitry shared with pulse generator 176, such that the TCC signals are transmitted using the pacing circuitry of pacemaker 100 and/or transmitted as sub-threshold pacing pulses or pacing pulses that occur during the refractory period of the heart.

In other examples, pacemaker 100 may include fewer or more components than the circuits and components shown in FIG. 3B. For instance, pacemaker 100 may include other physiological sensors and/or an RF telemetry circuit for communication with external device 40 instead of, or in addition to, TCC signal detector 175 and a TCC transmitter (if included).

Figure 4:
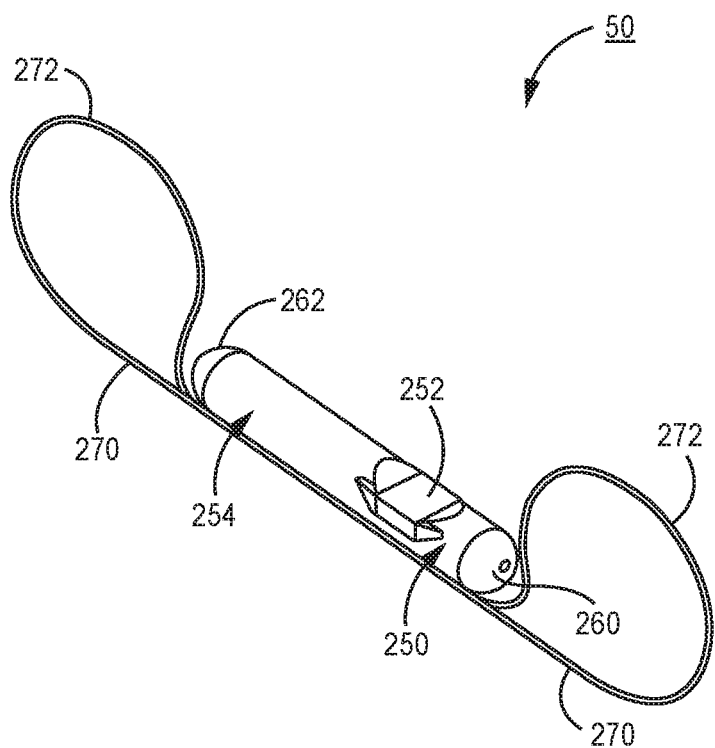
FIG. 4 illustrates a perspective view of a leadless pressure sensor according to one example.

FIG. 4 illustrates a perspective view of leadless pressure sensor 50 according to one example. Leadless pressure sensor 50 may generally correspond to the IMD disclosed in U.S. Pat. Publication No. 2012/0323099 A1 (Mothilal, et al.), incorporated herein by reference in its entirety. As shown in FIG. 4, pressure sensor 50 includes an elongated housing 250 having a pressure sensitive diaphragm or window 252 that exposes a pressure sensitive element within housing 250 to the surrounding pressure. Electrodes 260 and 262 may be secured to opposite ends of housing 250 and may be electrically insulated from housing 250 to form an electrode vector for receiving TCC signals. Electrodes 260 and 262 may be coupled to a TCC signal detector enclosed by housing 250. The TCC signal detector (which may also be referred to as a "TCC signal receiver") is configured to detect and demodulate TCC signals received from ICD 14 or 214.

Housing 250 may enclose a battery 254, a pressure sensing circuit, a TCC signal detector, control circuitry, and memory for storing pressure signal data. In some examples, the pressure sensing circuit includes an air gap capacitive element and associated circuitry, which may include temperature compensation circuitry, for producing a signal correlated to pressure along window 252. The pressure sensing circuit and window 252 may correspond to a pressure sensor module as generally disclosed in U.S. Pat. No. 8,720,276 (Kuhn, et al.), incorporated herein by reference in its entirety. The pressure sensing circuit may include a micro electro-mechanical system (MEMS) device in some examples. A fixation member 270 extends from housing 250 and may include a self-expanding stent or one or more self-expanding loops 272 that stabilize the position of pressure sensor 50 along an artery, such as the pulmonary artery, by gently pressing against the interior walls of the artery. When deployed in an arterial location, pressure sensor 50 produces and stores pressure signals correlated to arterial blood pressure.

Figure 6:
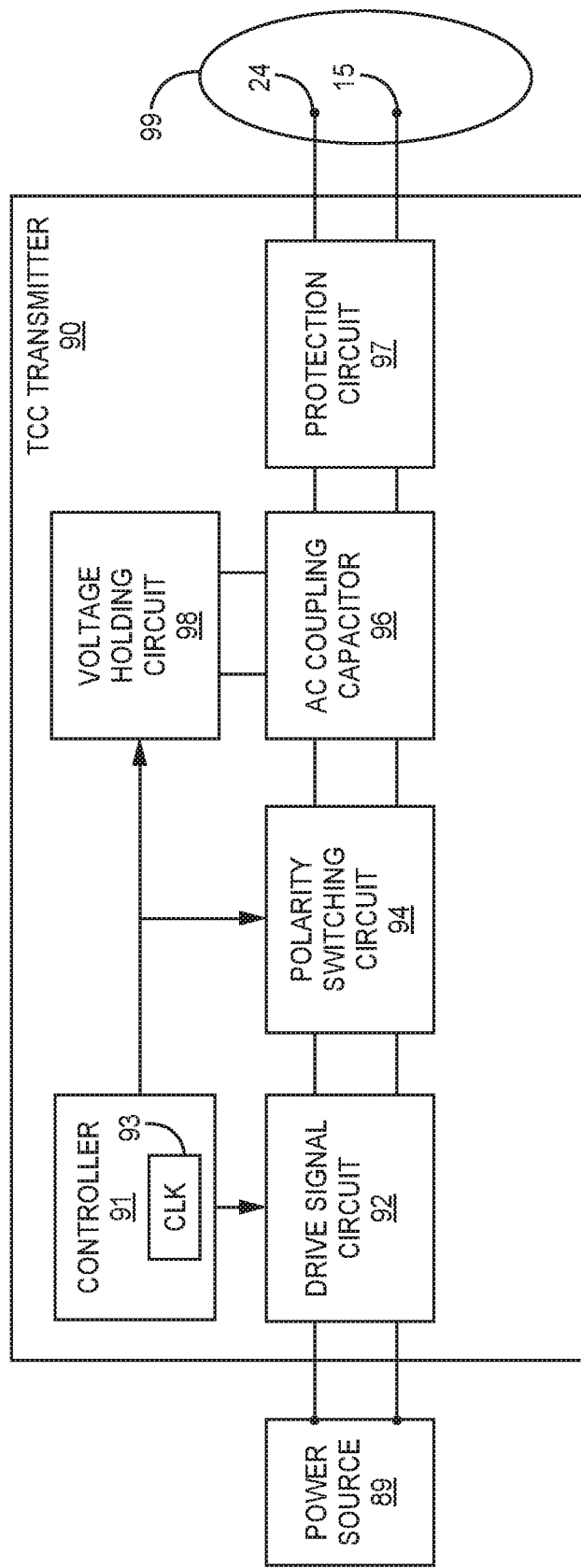
FIG. 6 is a conceptual diagram illustrating an example configuration of a TCC transmitter that may be included in the ICD of FIG. 5 or in the pacemaker of FIG. 3B or pressure sensor of FIG. 4.

In some examples, pressure sensor 50 includes a TCC transmitter, such as the transmitter shown in FIG. 6, for transmitting TCC signals to another medical device, such as ICD 14 or ICD 214, pacemaker 100 or external device 40. Pressure sensor 50 may transmit a pressure signal, data extracted from a pressure signal or other communication data in a TCC signal via electrodes 260 and 262 in some examples. For instance, pressure sensor 50 may include a TCC transmitter for at least producing acknowledgment and/or confirmation signals transmitted back to a transmitting device, e.g., ICD 14 or ICD 214, in response to receiving a TCC signal to confirm detection of a beacon signal and/or reception of transmitted data packets.

Figure 5:
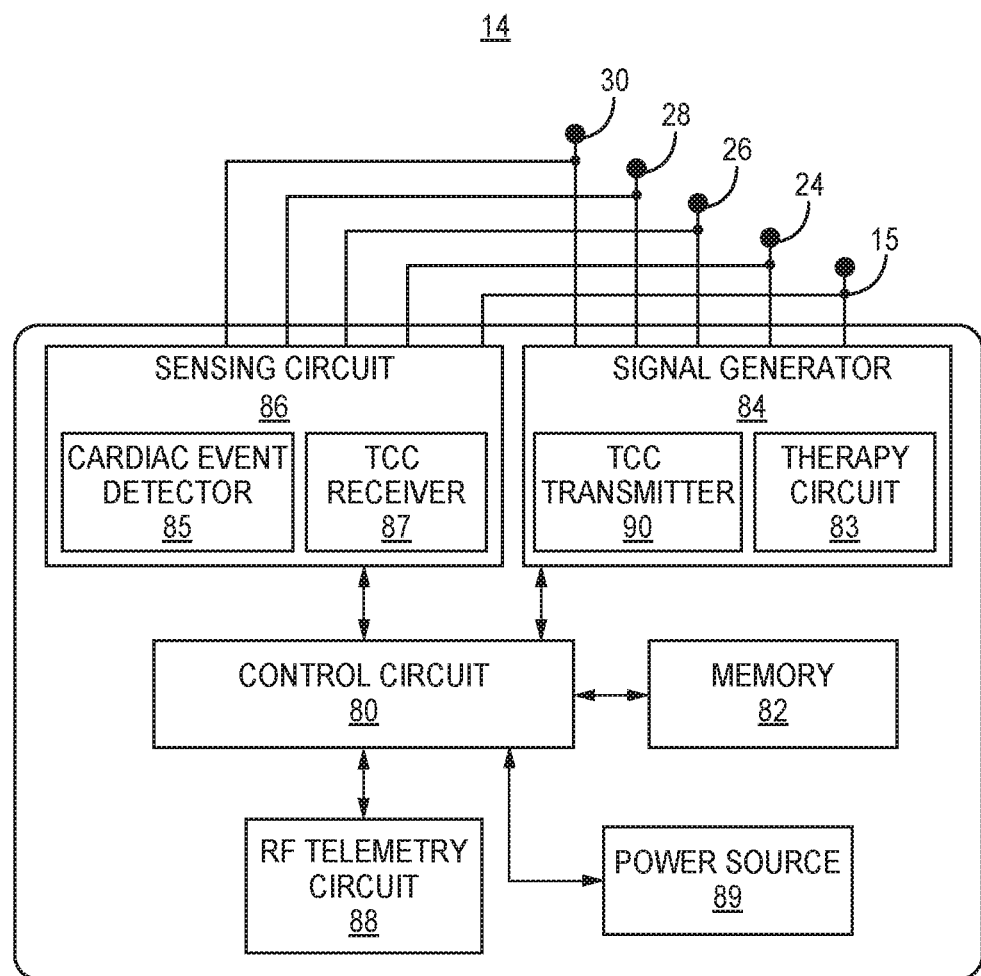
FIG. 5 is a schematic diagram of an ICD capable of transmitting TCC signals according to one example.

FIG. 5 is a schematic diagram of an ICD capable of transmitting TCC signals according to one example. For illustrative purposes, ICD 14 of FIG. 1 is depicted in FIG. 5 coupled to electrodes 24, 26, 28, and 30, with housing 15 represented schematically as an electrode. It is to be understood, however, that the circuitry and components shown in FIG. 5 may generally correspond to circuitry included in ICD 214 of FIG. 2 and adapted accordingly for single, dual, or multi-chamber cardiac signal sensing and therapy delivery functions using electrodes carried by transvenous leads. For instance, in the example of the multi-chamber ICD 214 of FIG. 2, signal generator 84 may include multiple therapy delivery output channels and sensing circuit 86 may include multiple sensing channels each selectively coupled to respective electrodes of RA lead 204, RV lead 206 and CS lead 208, corresponding to each cardiac chamber, e.g., the right atrium, the right ventricle, and the left ventricle.

The ICD circuitry may include a control circuit 80, memory 82, signal generator 84, sensing circuit 86, and RF telemetry circuit 88. A power source 89 provides power to the circuitry of the ICD, including each of the circuits 80, 82, 84, 86, and 88 as needed. Power source 89 may include one or more energy storage devices, such as one or more rechargeable or non-rechargeable batteries. The connections between power source 89 and each of the other circuits 80, 82, 84, 86 and 88 are to be understood from the general block diagram of FIG. 5 but are not shown for the sake of clarity. For example, power source 89 may be coupled to charging circuits included in signal generator 84 for charging capacitors or other charge storage devices included in therapy circuit 83 for producing electrical stimulation pulses such as CV/DF shock pulses and pacing pulses. Power source 89 is coupled to TCC transmitter 90 for providing power for generating TCC signals. Power source 89 provides power to processors and other components of control circuit 80, memory 82, amplifiers, analog-to-digital converters and other components of sensing circuit 86, and a transceiver of RF telemetry circuit 88, as examples.

Memory 82 may store computer-readable instructions that, when executed by a processor included in control circuit 80, cause ICD 14 to perform various functions attributed to ICD 14 (e.g., detection of arrhythmias, communication with pacemaker 100 or pressure sensor 50, and/or delivery of electrical stimulation therapy). Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Control circuit 80 communicates with signal generator 84 and sensing circuit 86 for sensing cardiac electrical activity, detecting cardiac rhythms, and controlling delivery of cardiac electrical stimulation therapies in response to sensed cardiac signals. The functional blocks shown in FIG. 5 represent functionality included in ICD 14 (or ICD 214) and may include any discrete and/or integrated electronic circuit components that implement analog and/or digital circuits capable of producing the functions attributed to ICD 14 herein. Providing software, hardware, and/or firmware to accomplish the described functionality in the context of any modern IMD system, given the disclosure herein, is within the abilities of one of skill in the art.

Sensing circuit 86 may be selectively coupled to electrodes 24, 26, 28, 30 and/or housing 15 in order to monitor electrical activity of the patient's heart 8. Sensing module 86 may include switching circuitry for selecting which of electrodes 24, 26, 28, 30 and housing 15 are coupled to sense amplifiers or other cardiac event detection circuitry included in cardiac event detector 85. Switching circuitry may include a switch array, switch matrix, multiplexer, or any other type of switching device suitable to selectively couple sense amplifiers to the selected electrodes. The cardiac event detector 85 within sensing circuit 86 may include one or more sense amplifiers, filters, rectifiers, threshold detectors, comparators, analog-to-digital converters (ADCs), or other analog or digital components configured to detect cardiac electrical events from a cardiac electrical signal received from heart 8.

In some examples, sensing circuit 86 includes multiple sensing channels for acquiring cardiac electrical signals from multiple sensing vectors selected from electrodes 24, 26, 28, 30 and housing 15. Each sensing channel may be configured to amplify, filter, digitize and rectify the cardiac electrical signal received from selected electrodes coupled to the respective sensing channel to improve the signal quality for sensing cardiac events, e.g., P-waves attendant to atrial depolarizations and/or R-waves attendant to ventricular depolarizations. For example, each sensing channel in sensing circuit 86 may include an input or pre-filter and amplifier for receiving a cardiac electrical signal developed across a selected sensing electrode vector, an analog-to-digital converter, a post-amplifier and filter, and a rectifier to produce a filtered, digitized, rectified and amplified cardiac electrical signal that is passed to a cardiac event detector 85 included in sensing circuit 86. The cardiac event detector 85 may include a sense amplifier, comparator or other circuitry for comparing the rectified cardiac electrical signal to a cardiac event sensing threshold, such as an R-wave sensing threshold amplitude, which may be an auto-adjusting threshold. Sensing circuit 86 may produce a sensed cardiac event signal in response to a sensing threshold crossing. The sensed cardiac events, e.g., R-waves and/or P-waves, are used for detecting cardiac rhythms and determining a need for therapy by control circuit 80. ICD 214 of FIG. 2 may include a sensing circuit having a separate atrial sensing channel for sensing P-waves using atrial electrodes and a ventricular sensing channel for sensing R-waves using ventricular electrodes.

Control circuit 80 may include interval counters, which may be reset upon receipt of a cardiac sensed event signal from sensing circuit 86. The value of the count present in an interval counter when reset by a sensed R-wave or P-wave may be used by control circuit 80 to measure the durations of R-R intervals, P-P intervals, P-R intervals and/or R-P intervals, which are measurements that may be stored in memory 82. Control circuit 80 may use the count in the interval counters to detect a tachyarrhythmia event, such as atrial fibrillation (AF), atrial tachycardia (AT), VF or VT. These intervals may also be used to detect the overall heart rate, ventricular contraction rate, and heart rate variability.

Signal generator 84 includes a therapy circuit 83 and a TCC transmitter 90. The therapy circuit 83 is configured to generate cardiac electrical stimulation pulses, e.g., CV/DF shock pulses and cardiac pacing pulses for delivery to heart 8 via electrodes carried by lead 16 (and in some cases housing 15). Signal generator 84 may include one or more energy storage elements, such as one or more capacitors, configured to store the energy required for a therapeutic CV/DF shock or pacing pulse. In response to detecting a shockable tachyarrhythmia, control circuit 80 controls therapy circuit 83 to charge the energy storage element(s) to prepare for delivering a CV/DF shock. Therapy circuit 83 may include other circuitry, such as charging circuitry, which may include a transformer and/or charge pump, to charge the energy storage element, and switches to couple the energy storage element to an output capacitor to discharge and deliver the CV/DF shock and change the polarity of the shock to provide a bi-phasic or multi-phasic shock. Therapy circuit 83 may include a variety of voltage level-shifting circuitry, switches, transistors, diodes, or other circuitry. Therapy circuit 83 may include switching circuitry for selecting a shock delivery vector and delivers the shock therapy to the patient's heart 8 via the shock delivery vector, e.g., two or more electrodes such as defibrillation electrode 24 or 26 and housing 15.

In some examples, therapy circuit 83 may include both a low voltage therapy circuit for generating and delivering relatively low voltage therapy pulses, such as pacing pulses, and a high voltage therapy circuit for generating and delivering CV/DF shocks. Low voltage pacing pulses may be delivered via a pacing electrode vector selected from electrodes 24, 26, 28, 30 and housing 15. Pacing pulses may be delivered when a pacing escape interval set by a pace timing circuit of control circuit 80 times out without a sensed cardiac event causing the escape interval to be reset. The pace timing circuit may set various escape intervals for timing pacing pulses, e.g., to provide bradycardia pacing or post-shock pacing, or in response to detecting a tachyarrhythmia for delivering ATP. In some examples, pacemaker 100 is provided for delivering at least some low voltage pacing therapies, e.g., when signaled to do so by a TCC signal transmitted from ICD 14. A low voltage therapy circuit included in ICD 214 of FIG. 2 may include multiple pacing channels, including an atrial pacing channel, a right ventricular pacing channel, and a left ventricular pacing channel, to provide single, dual or multi-chamber pacing in addition to the high voltage therapy circuit used for delivering CV/DF shocks.

In some examples, ICD 14 (or ICD 214) is configured to monitor the impedance of an electrode vector. For example, signal generator 84 may apply a current drive signal to a pair of electrodes coupled to ICD 14. Sensing circuit 86 may detect the resulting voltage developed across the pair of electrodes. Impedance monitoring may be performed for detecting a lead or electrode issue and for selecting a therapy delivery electrode vector, a TCC transmitting electrode vector, or a sensing electrode vector based at least in part on the lead/electrode impedance. In other examples, ICD 14 or ICD 214 may be configured to monitor bioimpedance in a tissue volume, e.g., thoracic impedance or cardiac impedance, for monitoring a patient condition.

TCC transmitter 90 is configured to generate TCC signals for transmission from a transmitting electrode vector selected from the electrodes 24, 26, 28, 30 and housing 15 via a conductive tissue pathway. TCC transmitter 90 is configured to generate and transmit a TCC signal, e.g., to communicate with pacemaker 100, sensor 50 or another IMD, or an external device 40. In some examples, signal generator 84 includes switching circuitry for selectively coupling TCC transmitter 90 to a selected transmitting electrode vector, e.g., using any two or more of electrodes 24, 26, 28 30 and housing 15, e.g., housing 15 and defibrillation electrode 24, for transmission of a TCC signal.

The TCC signal may be transmitted having a carrier signal with a peak-to-peak amplitude and carrier frequency selected to avoid stimulation of excitable tissue of patient 12. In some examples, the carrier frequency of the TCC signal may be 100 kilohertz (kHz) or higher. A TCC signal emitted or received, for example by electrode 24 and housing 15, at a frequency of at least approximately 100 kHz may be less likely to stimulate nearby tissue, e.g., muscles or nerves, or cause pain than lower frequency waveforms. Consequently, a TCC signal having a frequency of at least approximately 100 kHz may have a higher amplitude than a lower frequency signal without causing extraneous nerve or muscle stimulation. A relatively higher amplitude signal may increase the likelihood that pacemaker 100, pressure sensor 50 or another implanted or external device, may receive the TCC signal from ICD 14 (or ICD 214). The peak-to-peak amplitude of the TCC signal may be within a range from approximately 100 microamps to 10 milliamps (mA) or more, such as within a range from approximately 1 mA to approximately 10 mA. In some examples, the amplitude of the TCC signal may be approximately 3 mA. A TCC signal having a frequency of at least approximately 100 kHz and an amplitude no greater than approximately 10 mA may be unlikely to stimulate nearby tissue, e.g., muscles or nerves, or cause pain. For a transmitting electrode vector having an impedance of 200 ohms injecting a current signal having an amplitude of 10 mA peak-to-peak, the voltage signal at the transmitting electrode vector may be 2 Volts peak-to-peak. The voltage developed at the receiving electrode vector may be in the range of 0.1 to 100 millivolts peak-to-peak.

The modulation of the TCC signal may be, as examples, amplitude modulation (AM), frequency modulation (FM), or digital modulation (DM), such as frequency-shift keying (FSK) or phase-shift keying (PSK). In some examples, the modulation is FM toggling between approximately 150 kHz and approximately 200 kHz. In some examples, the TCC signal has a frequency of 150/200 kHz and is modulated using FSK modulation at 12.5 kbps. In the illustrative examples presented herein a TCC signal having a carrier frequency of 100 kHz is modulated to encode data using binary phase shift keying (BPSK). Balanced pulses of opposite polarity are used to shift the phase of the TCC signal, e.g., by 180 degrees positively or negatively, and balance the charge injected into the body tissue during the phase shift to minimize the likelihood of interfering with cardiac event sensing operations of the cardiac event detector 85. The BPSK data modulated on TCC signals, e.g., being sent to pacemaker 100 or pressure sensor 50, may include "wake up" commands, commands to deliver a therapy, and/or commands to collect or send physiological signal data, as examples.

The configuration of signal generator 84 including TCC transmitter 90 illustrated in FIG. 5 may provide "one-way" or uni-directional TCC. Such a configuration may be used if, for example, the ICD 14 is configured as a control device to transmit a command or request to another IMD configured as a responder, e.g., to pacemaker 100 or sensor 50 to provide commands for pacing delivery or pressure signal acquisition, for instance. In some examples, sensing circuit 86 may include a TCC receiver 87 to facilitate "two-way" TCC between the ICD and another IMD. ICD 14 or ICD 214 may be configured to receive confirmation signals from the intended receiving device to confirm that a transmitted TCC signal was successfully received. In other examples, ICD 14 or ICD 214 may receive commands via TCC receiver 87 from another IMD or external device. The TCC receiver 87 may have more sensitivity than an RF telemetry circuit 88, e.g., to compensate for lower signal-to-noise ratio signals from a transmitting device such as pacemaker 100 or sensor 50. For instance, pacemaker 100 may generate relatively low signal-to-noise ratio signals by generating relatively small amplitude signals due to its smaller power source, and/or to avoid stimulation of adjacent cardiac tissue. A modulated or unmodulated carrier signal may be received by TCC receiver 87 via electrodes selectively coupled to sensing circuit 86. TCC receiver 87 may include an amplifier, filter and demodulator to pass the demodulated signal, e.g., as a stream of digital values, to control circuit 80 for decoding of the received signal and further processing as needed.

In other examples, TCC receiver 87 and/or TCC transmitter 90 may be distinct components separate from sensing circuit 86 and signal generator 84, respectively. For example, ICD 14 may include a TCC transceiver that incorporates the circuitry of TCC receiver 87 and/or TCC transmitter 90. In this case, the functionality described with respect to TCC receiver 87 and/or TCC transmitter 90 may be performed via a distinct TCC component instead of being part of sensing circuit 86 and signal generator 84.

Memory 82 may be configured to store a variety of operational parameters, therapy parameters, sensed and detected data, and any other information related to the monitoring, therapy and treatment of patient 12. Memory 82 may store, for example, thresholds and parameters indicative of tachyarrhythmias and/or therapy parameter values that at least partially define delivered anti-tachyarrhythmia shocks and pacing pulses. In some examples, memory 82 may also store communications transmitted to and/or received from pacemaker 100, pressure sensor 50 or another device.

ICD 14 may have an RF telemetry circuit 88 including an antenna and transceiver for RF telemetry communication with external device 40. RF telemetry circuit 88 may include an oscillator and/or other circuitry configured to generate a carrier signal at the desired frequency. RF telemetry circuit 88 further includes circuitry configured to modulate data, e.g., stored physiological and/or therapy delivery data, on the carrier signal. The modulation of RF telemetry signals may be, as examples, AM, FM, or DM, such as FSK or PSK.

In some examples, RF telemetry circuit 88 is configured to modulate the TCC signal for transmission by TCC transmitter 90. Although RF telemetry circuit 88 may be configured to modulate and/or demodulate both RF telemetry signals and TCC signals within the same frequency band, e.g., within a range from approximately 150 kHz to approximately 200 kHz, the modulation techniques for the two signals may be different. In other examples, TCC transmitter 90 includes a modulator for modulating the TCC signal and/or TCC receiver 87 includes a demodulator for modulating the TCC signal rather than RF telemetry circuit 88.

FIG. 6 is a conceptual diagram of TCC transmitter 90 (or transmitter portion of a transceiver) according to one example. TCC transmitter 90 may include a controller 91, a drive signal circuit 92, polarity switching circuit 94, alternating current (AC) coupling capacitor 96, protection circuit 97, and voltage holding circuit 98. In other examples, TCC transmitter 90 may include fewer or more components than the circuits and components shown in FIG. 6. ICD power source 89 is shown coupled to TCC transmitter 90 to provide power necessary to generate TCC signals. While the controller 91, drive signal circuit 92, polarity switching circuit 94, AC coupling capacitor 96, protection circuit 97, and voltage holding circuit 98 are shown as discrete circuits by the blocks in FIG. 6, it is recognized that these circuits may include common components or a common circuit may perform the functions attributed to the separate circuit blocks shown in FIG. 6. For example, generating a carrier current signal having a carrier frequency and a peak-to-peak amplitude may be performed by drive signal circuit 92 and/or polarity switching circuit 94 under the control of controller 91.

Controller 91 may include a processor, logic circuitry, data registers, a clock circuit and/or other circuitry or structures for providing the functionality attributed to controller 91 herein. Controller 91 may include a dedicated clock circuit 93 for generating clock signals used to control the frequency of the transmitted TCC signals. In other examples, controller 91 may be implemented within control circuit 80. The clock circuit 93 may be configured to provide a clock signal that may be used to transmit the TCC signal during a transmission session using more than one frequency. For example, TCC transmitter 90 may be configured to provide a clock signal that may be used to transmit the TCC signal using at least three different frequencies, the TCC signal being modulated using FSK during a wakeup mode (e.g., modulating the signal using two different frequencies) and switch to a data transmission mode that includes transmitting data packets using a carrier signal at a third frequency (e.g., modulated using BPSK or other modulation technique) For example, during the wakeup mode a beacon signal may be transmitted using high and low alternating frequencies, which may be centered on the frequency of the carrier signal. The beacon signal may be followed by a request to establish a communication, sometimes referred to as an "OPEN" request or command, transmitted at the carrier frequency. A clock signal generated by clock circuit 93 may be required to enable generation of at least three different frequencies of the TCC signal produced by drive signal circuit 92 and/or polarity switching circuit 94 and passed to AC coupling capacitor 96 in this particular example.

After switching from the wakeup mode to the transmission mode, the TCC transmitter 90 may be configured to transmit the TCC signal at the carrier frequency, different than the distinct high and low frequencies used during the beacon signal transmission. The carrier signal is modulated using BPSK in one example such that the TCC signal is transmitted using a single frequency during the data transmission mode.

The clock circuit 93 may operate at one clock frequency during the wakeup mode and at another clock frequency during the data transmission mode. For example, clock circuit 93 may be controlled to operate at the lowest possible clock frequency that can be used to generate the high frequency and low frequency cycles of the beacon signal during the wakeup mode to conserve power provided by power source 89. The clock circuit 91 may be configured to operate at a higher frequency for controlling drive signal circuit 92 and/or polarity switching circuit 94 to generate the carrier signal during signal transmission. The clock circuit frequency may be changed between the wakeup and transmission modes under the control of controller 91 using digital trim codes stored in hardware registers.

TCC transmitter 90 is shown coupled to a transmitting electrode vector 99 including defibrillation electrode 24 and housing 15 (of FIG. 1) in this example. It is to be understood that TCC transmitter 90 may be coupled to one or more TCC transmitting electrode vectors selected from any of the available electrodes coupled to the transmitting device as described above via switching circuitry included in signal generator 84. Controller 91 may be configured to switchably connect a transmitting electrode vector 99 to TCC transmitter 90 for transmission of TCC signals. For example, controller 91 may control switches included in signal generator 84, which may be included in TCC transmitter 90 between AC coupling capacitor 96 and transmitting electrode vector 99, e.g., in protection circuit 97. Controller 91 may be configured to select a transmitting electrode vector from among multiple electrodes coupled to the transmitting device, which may include electrodes carried by the housing of the transmitting device, a transvenous lead, e.g., any of leads 204, 206 or 208 shown in FIG. 2, or a non-transvenous lead, e.g., extra-cardiovascular lead 16 shown in FIG. 1.

Drive signal circuit 92 may include a voltage source and/or a current source powered by power source 89. In one example, drive signal circuit 92 may be an active drive signal circuit generating a balanced, bi-directional drive current signal to balance the return current with the drive current for a net zero direct current (DC) current injected into the body tissue via transmitting electrode vector 99. In another example, the drive signal circuit 92 may include a charge pump and a holding capacitor that is charged by the charge pump to generate a current signal that is coupled to the transmitting electrode vector 99. In yet another example, drive signal circuit 92 may include a current source that is used to charge a holding capacitor included in drive signal circuit 92.

The drive signal generated by drive signal circuit 92 may be a voltage signal in some examples. In the illustrative examples presented herein, the drive signal circuit 92 generates a current signal to deliver TCC signal current through the transmitting electrode vector 99 having a desired peak-to-peak amplitude, e.g., high enough to produce a voltage signal on receiving electrodes of a receiving device that is detectable by the receiving device, which may be pacemaker 100, sensor 50 or another intended receiving medical device, implanted or external. The peak-to-peak current amplitude is low enough to avoid or minimize the likelihood of stimulation of tissue. A carrier signal that may be generated by drive signal circuit 92 and/or polarity switching circuit 94 may have a peak-to-peak amplitude in a range from approximately 1 mA to approximately 10 mA, such as approximately 3 mA peak-to-peak, as discussed above. The voltage developed at the receiving electrode vector may be in the range of 0.1 to 100 millivolts peak-to-peak.

Polarity switching circuit 94 receives the drive current signal from drive signal circuit 92 and includes circuitry configured to switch the polarity of the drive signal current at a carrier frequency of the TCC signal. For example, polarity switching circuit 94 may include transistors and/or switches configured to switch the polarity of the drive current signal at the carrier frequency of the TCC signal. In some examples, polarity switching circuit 94 includes a respective one or more transistors and/or switches, and the on-off states of the respective transistor(s) and/or switch(es) are alternated to switch the polarity of the drive current signal at the carrier frequency. In this way, the TCC signal is transmitted having a carrier frequency defined by a carrier frequency cycle length in which the transmitted signal has a first polarity pulse for a first half of the carrier frequency cycle length and a second opposite polarity pulse for the second half of the carrier frequency cycle length. Each of the first and second pulses each inject a half-cycle charge (of opposite polarity) via the transmitting electrode vector 99 such that a net zero DC current is injected into the body tissue during carrier frequency signal transmission. As discussed above, the carrier frequency may be approximately 100 kHz. For example, the carrier frequency may be within a range from approximately 33 kHz to approximately 250 kHz.

In some examples, RF telemetry module 86 may include a mixed signal integrated circuit or other circuitry configured to provide a digital version of the modulated TCC signal to controller 91. In other examples, controller 91 is configured to produce the digital input signal for modulating the TCC carrier signal to encode communication data in the transmitted signal. Controller 91 controls one or both of drive signal circuit 92 and/or polarity switching circuit 94 to modulate the TCC carrier frequency signal to generate the modulated TCC signal with an amplitude, phase shifts and/or frequency according to the encoding. For example, controller 91 may control polarity switching circuit 94 to toggle the frequency of the carrier signal according to FSK modulation to encode the communication data. In another example, controller 91 may control polarity switching circuit 94 to switch the polarity of the current signal after a desired portion of the carrier frequency cycle length to shift the phase of the AC current signal by 180 degrees according to BPSK modulation. Techniques for generating a modulated TCC signal that avoids or minimizes interference with a sensing circuit, e.g., sensing circuit 86, are described below in conjunction with FIGS. 7A through 12.

Polarity switching circuit 94 is capacitively coupled to the transmitting electrode vector 99 (e.g., electrode 24 and housing 15 in the example shown) via AC coupling capacitor 96. AC coupling capacitor 96 couples the current signal output from polarity switching circuit 94 to the transmitting electrode vector 99 to inject the current into the conductive body tissue pathway. AC coupling capacitor 96 may include one or more capacitors coupled in series with one or each of the electrodes included in electrode vector 99. AC coupling capacitor 96 is charged to a DC operating voltage at the beginning of a TCC signal. AC coupling capacitor 96 is selected to have a minimum capacitance that is based on the frequency and the peak-to-peak current amplitude of the carrier signal being used to transmit beacon and data signals. As examples, AC coupling capacitor 96 may have a capacitance of at least one nanofarad and up to ten microfarads for coupling a carrier signal having a frequency between 25 kHz and 250 kHz and peak-to-peak current amplitude of 100 microamps to 10 milliamps. Larger capacitances may be used but may increase the time required to charge the AC coupling capacitor to a DC operating voltage.

During a "cold start," e.g., at the beginning of a TCC transmission session when AC coupling capacitor 96 is uncharged, the charging of AC coupling capacitor 96 to the DC operating voltage may result in a low frequency current being injected into the body through the transmitting electrode vector. This low frequency current is more likely to interfere with the operation of cardiac event detector 85 or other electrophysiological sensing circuits included in co-implanted IMDs or external devices coupled to the patient. Cardiac event detector 85 and other electrophysiological sensing circuits of intended or unintended receiving devices may operate in a low frequency band, e.g., 1 to 100 Hz. As such, low frequency artifact at the start of TCC signal transmission, during charging of the AC coupling capacitor 96, may interfere with cardiac event detector 85. After the DC operating voltage is established on AC coupling capacitor 96, the high frequency carrier signal, e.g., 100 kHz, is typically above the operating bandwidth of cardiac event detector 85 and other electrophysiological sensing circuitry of the IMD system and unlikely to cause interference or false event detection.

TCC transmitter 90 may include a voltage holding circuit 98 coupled to AC coupling capacitor 96. Voltage holding circuit 98 may be controlled to hold the AC coupling capacitor 96 at the DC operating voltage between transmitted TCC signals during a TCC transmission session and/or between TCC transmission sessions. By holding the AC coupling capacitor 96 at a DC voltage during time intervals between TCC signal transmissions, interference with sensing circuitry that may otherwise occur due to the low frequency artifact injected during charging of the AC coupling capacitor 96 to the DC operating voltage is minimized or avoided.

Examples of circuitry included in voltage holding circuit 98 are described in U.S. Patent Application No. 62/591,806 (Peichel, et al.), incorporated herein by reference in its entirety. In some examples voltage holding circuit 98 may include circuitry for floating AC coupling capacitor 96 at the DC voltage between TCC signal transmissions. In other examples, voltage holding circuit 98 may include circuitry to actively hold the AC coupling capacitor 96 at a DC voltage between TCC signal transmissions. A variety of circuitry may be conceived for preventing or minimizing discharging of AC coupling capacitor 96 between TCC signal transmissions. In this way, at the start of transmitting the next TCC signal packet, the AC coupling capacitor 96 is already at or near the DC operating voltage. Without having to re-establish the DC voltage on the AC coupling capacitor 96, low frequency artifact injected into the TCC tissue pathway at the onset of the next data packet transmission is avoided or minimized. It is recognized that leakage currents may still exist within TCC transmitter 90 and may cause some discharge of AC coupling capacitor 96 between signal transmissions. Voltage holding circuit 98 may be used to minimize any discharge of AC coupling capacitor 96 between transmitted TCC signals to minimize low frequency interference with sensing circuit 86 (FIG. 5) of the transmitting device as well as sensing circuits of other co-implanted IMDs and/or external device coupled to the patient.

Figure 7A:
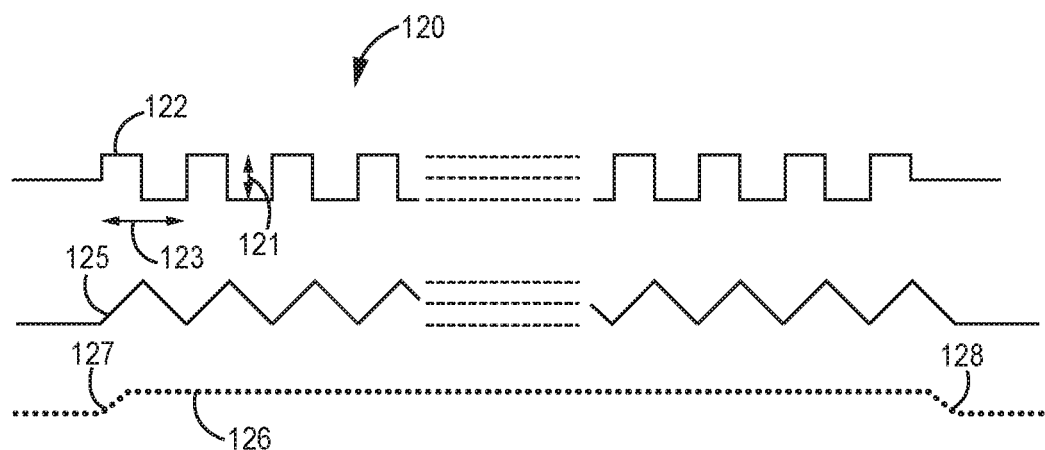
FIGS. 7A and 7B are conceptual diagrams of transmitted TCC signals and the DC voltage shift that may occur at a receiving electrode vector at the onset and end of the transmitted TCC signals.
Figure 7B:
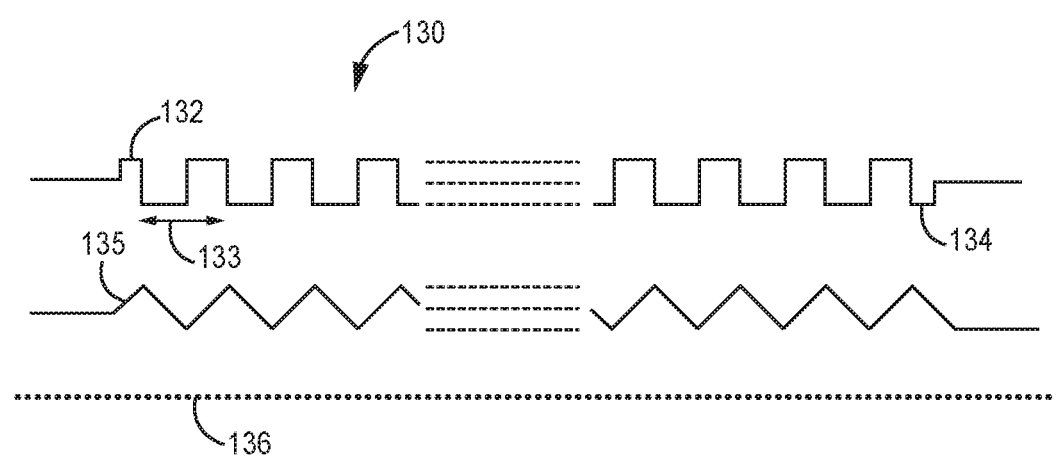

FIGS. 7A and 7B are conceptual diagrams of transmitted TCC signals and the DC voltage shift that may occur at a receiving electrode vector at the onset and end of the transmitted TCC signals. In FIG. 7A, the transmitted TCC signal 120 is shown as a carrier signal having a peak-to-peak amplitude 121 and carrier frequency cycle length 123. Each half-cycle pulse 122 of the carrier frequency signal delivers a half cycle charge that is dependent on the pulse duration, which is half of the cycle length 123, and its peak amplitude, which is half of the peak-to-peak amplitude 121. The net half cycle charge injected after one half-cycle of the carrier signal may result in a net DC voltage shift at a receiving electrode vector. For example, a sensing electrode vector coupled to cardiac event detector 85 may be an unintended receiving electrode vector of the TCC signal 120. The received TCC signal 120 may be low pass filtered by an input filter of the sensing circuit 86 resulting in a low pass filtered input signal 125 that may be passed to cardiac event detector 85. The average DC voltage signal 126 of the low pass filtered input signal 125 includes a DC voltage shift 127 occurring during the first half cycle pulse 122 that may cause interference with cardiac event detection. At the end of the TCC signal 120, the average DC voltage signal 126 of low pass filtered signal 125 includes a DC voltage shift 128, which may also interfere with cardiac event detection.

In FIG. 7B, the TCC signal 130 is started with a pulse 132 and ended with a pulse 134 that each have a pulse duration that is one-quarter of the carrier frequency cycle length 133. In this case, the average DC voltage signal 136 of the low-pass filtered input signal 135 does not include a DC voltage shift (or only a negligible DC voltage shift). The TCC signal 130 does not interfere with cardiac event sensing by cardiac event detector 85. As such, even though carrier signal 120 may be transmitted as a charge-balanced signal in FIG. 7A, DC voltage shifts 127 and 128 may occur in the average DC voltage signal 126 of the low pass filtered signal 125 passed to cardiac event detector 85. By starting and ending the TCC signal 130 with pulses having a net charge that is less than the half cycle charge of the carrier signal, e.g., by transmitting one-quarter cycle length pulses 132 and 134 at the start and end of TCC signal 130, respectively, DC voltage shifts are avoided or minimized. The TCC signal 130 may be a modulated or unmodulated carrier signal transmitted as a beacon signal by transmitter 90 during a wakeup mode. In other examples, TCC signal 130 may represent a modulated carrier signal transmitted as a data packet during a data transmission mode of transmitter 90. In yet other examples, the TCC signal 130 may represent an acknowledgment signal transmitted from the receiving device to a transmitting device to confirm detection of a beacon signal or receipt of data signals.

Referring again to FIG. 6, the drive signal circuit 92 and/or polarity switching circuit 94 may be controlled by controller 91 to start and end a TCC signal with a starting pulse and an ending pulse each having a net charge that is less than the half cycle charge of the carrier signal. For example, by delivering a starting pulse having a net charge that is one-quarter the cycle charge of the carrier signal, the net charge injected via the transmitting electrode vector 99 is quickly balanced during the next, second pulse of the TCC signal, which has the opposite polarity of the starting pulse and a pulse width that is half of the carrier signal cycle length. Any DC voltage shift at a receiving electrode vector is reduced, avoided or minimized.

The TCC transmitter 90 may include protection circuit 97 that allows the delivery of the TCC signal via electrodes coupled to other ICD circuitry but protects the TCC transmitter 90 and other circuitry of the ICD 14 from voltages that may develop across the electrodes, e.g., during a CV/DF shock delivered by therapy circuit 83 or an external defibrillator as well as high voltages that may develop across the TCC transmitting electrode vector during other situations such as an electrocautery procedure or magnetic resonance imaging. The circuitry within housing 15 of ICD 14 protected by protection circuit 97 may include circuitry of any of the components of ICD 14 illustrated in FIG. 5, such as control circuit 80, memory 82, sensing circuit 86, signal generator 84, and RF telemetry circuit 88.

Protection circuit 97 may be coupled between drive signal circuit 92 and the transmitting electrode vector 99, e.g., between AC coupling capacitor 96 and electrode 24 and housing 15 as shown. In some examples, protection circuit 97 may include circuitry before and/or after AC coupling capacitor 96. Protection circuit 97 may include, as examples, capacitors, inductors, switches, resistors, and/or diodes. Examples of TCC signal generation and protection circuitry that may be utilized in conjunction with the signal transmission techniques disclosed herein are generally described in U.S. Pat. No. 9,636,511 (Carney, et al.), incorporated herein by reference in its entirety.

In some examples, TCC transmitter 90 may be controlled by control circuit 80 to transmit data via TCC multiple times throughout a cardiac cycle. In some cases, multiple transmissions at different times during the cardiac cycle increase the likelihood that the data is sent during both systole and diastole to make use of cardiac motion to increase the chance that the intended receiving electrode vector, such as housing-based electrodes of pacemaker 100 or pressure sensor 50, is orientated in a non-orthogonal position relative to the transmitting electrode vector. Multiple transmissions at different times during the cardiac cycle may thereby increase the likelihood that that the transmitted packet is received. While TCC transmitter 90 is shown coupled to a transmitting electrode bipole (vector 99) in FIG. 6, it is to be understood that multiple transmitting electrode vectors may be coupled to TCC transmitter 90 for transmitting a TCC current signal along multiple conductive tissue pathways for reception by multiple receiving electrode vectors or to increase the likelihood of being received by a single receiving electrode vector.

FIG. 8 is a conceptual diagram of a TCC transmission session 300 that may be executed by TCC transmitter 90 under the control of control circuit 80. TCC transmission session 300 includes a plurality of TCC signals that are transmitted. The challenges of transmitting encoded information in a TCC signal include avoiding unintentional electrical stimulation of nerve and muscle tissue, including myocardial tissue, and avoiding or minimizing interference with sensing circuitry included in one or more devices of the IMD system performing TCC while still successfully transmitting information in a time efficient and power efficient manner. Techniques disclosed herein include a method for transmitting a wakeup signal to a receiving device followed by transmission of encoded data in a manner that minimizes or avoids interference with electrical signal sensing circuitry or the transmitting device and/or an intended or unintended receiving device.

Transmission session 300 may include a wakeup mode 310 in which one or more TCC signals are transmitted followed by data transmission mode 311 that may include transmission of one or more TCC signals as data packets 330. In other instances, transmission session 300 does not include a wakeup mode. In the illustrative examples described herein, a group of bits of encoded data is referred to as a data "packet." In some uses, the term "packet" may imply that transmitted data is guaranteed to be received along a communication pathway without error and a confirmation signal indicating receipt without error maybe returned from the intended receiving device. In some applications, a group of bits of encoded data may be referred to as a "datagram" when transmission of the encoded data occurs without guarantee that the data reaches the intended receiver and without certainty that transmission errors did not occur. Groups of bits of encoded data 330 are referred to as "packets" herein, however, it is recognized that in some clinical applications the groups of bits 330 may be transmitted as datagrams, without guarantee that the receiving device actually received the data error-free.

Each transmission session 300 may, in some instances, begin with a wakeup mode 310, as further described in conjunction with FIG. 9, followed by at least one data packet 330. Multiple data packets 330 may be transmitted and assembled into a stream of data by the receiving device. In examples that include bi-directional communication, the transmitting device may toggle between data transmission, during which one data packet 330 is transmitted, and a receiving window 350 between data packets, during which the transmitting device waits for a response from the intended receiver, e.g., a signal confirming receipt of the transmitted packet, requested data sent back to the transmitter or other requested response to the received data packet. Examples of the structure of each data packet 330 are described below, e.g., in conjunction with FIG. 10.

FIG. 9 is a diagram of one example of operations performed during the wakeup mode 310 by an IMD system, e.g., system 10 of FIG. 1 or system 200 of FIG. 2, according to one example. Functions performed by the transmitting device (TRN) are represented above the dashed line. Functions performed by the receiving device (RCV) are performed below the dashed line. In the example of ICD 14 (or ICD 214) being the transmitting device, control circuit 80 controls TCC transmitter 90 to transmit one or more TCC signals, such as beacon signals 312. In the example of pacemaker 100 being the receiving device, control circuit 170 may power up TCC signal detector 175 (shown in FIG. 3B) periodically for a beacon search period 320 to detect the beacon signal 312.

In some examples, the beacon signal 312 may be transmitted multiple times as needed until a response is received from the receiving device. In the example shown, the beacon signal 312 is sent four times, each time followed by a receiving period 314 for waiting for acknowledgement signal 328 transmitted from the receiving device to confirm detection of the beacon signal 312. In response to receiving the acknowledgement signal 328 as indicated at arrow 316, the transmitter 90 stops transmitting the beacon signal 312 and switches from the wakeup mode 310 to the transmission mode 311 as shown in FIG. 8.

If the transmitting device includes a sensing circuit, such as sensing circuit 86, the first (leftmost) beacon signal 312 may be started during a blanking period 304 applied to the sensing circuit 86 following a cardiac event 302. At the start of a transmission session, the early cycles of the carrier signal establish a DC voltage across the AC coupling capacitor 96. During this time, a low frequency current may be injected into the body tissue conductive pathway via the TCC transmitting electrode vector. The low frequency current is more likely to cause interference with cardiac event detector 85 of sensing circuit 86 (or other electrical signal sensing circuits of other implanted devices) than the relatively high carrier frequency of the TCC signal. By starting the first signal, e.g., leftmost beacon signal 312, of each transmission session during a blanking period 304 applied to the sensing circuit 86 of the transmitting device, the DC voltage is established on the AC coupling capacitor 96 mostly or entirely during the blanking period 304 when the cardiac event detector 85 is blanked and relatively immune to the low frequency artifact.

The blanking period 304 may be an automatic blanking period that the control circuit 80 applies to the cardiac event detector 85 following an intrinsic or paced cardiac event 302. Cardiac event 302 may be an intrinsic cardiac event sensed by the cardiac event detector 85, and blanking period 304 may be a post-sense blanking period set in response to detecting the intrinsic cardiac event, e.g., an R-wave or P-wave. For example, a post-sense blanking period may be applied to a sense amplifier or other cardiac event detection circuitry of sensing circuit 86 in response to a cardiac event sensing threshold crossing. At other times, cardiac events 302 may be pacing pulses delivered at a pacing interval 306, in which case blanking period 304 is a post-pace blanking period automatically applied to the sensing circuit 86 upon delivery of the pacing pulse by therapy circuit 83. A post-pace or post-shock blanking period may be applied to prevent saturation of the sense amplifier(s) of sensing circuit 86 during delivery of a pacing pulse or cardioversion/defibrillation shock. An automatic post-sense or post-pace blanking period may be in the range of 50 to 200 ms, for example 150 ms.

When blanking period 304 is a post-sense or post-pace blanking period, transmission of the first beacon signal 312 may be held in a pending state until blanking period 304 is started. In another example, blanking period 304 is a communication blanking period set by control circuit 80 to enable initiation of the first beacon signal 312 at any time during the cardiac cycle, independent of the cardiac cycle and cardiac event timing. Blanking period 304 is not necessarily shown scaled in time relative to TCC signals 312 and 330 and may be up to 150 to 200 ms long in some examples. It is recognized, however, that when TCC transmitter 90 and therapy circuit 83 of the transmitting ICD 14 or ICD 214 share an electrode vector and/or pulse generation circuitry of signal generator 84, TCC signal transmission may not occur simultaneously with a cardiac electrical stimulation therapy pulse. TCC signal transmission is generally performed at distinctly separate times from therapy delivery since the TCC transmitting electrode vector may provide an inappropriate return path for stimulation energy being delivered by a therapy delivery electrode vector.

Low frequency current may be injected into body tissue at the beginning of a TCC carrier signal transmission, such as beacon signal 312, as the AC coupling capacitor 96 is charged to a DC operating voltage. This low frequency artifact is not detected as a cardiac event by cardiac event detector 85 during a blanking period 304. Furthermore, during a post-sense, post-pace or post-shock blanking period, myocardial tissue is in a state of physiological refractoriness such that any low frequency signal injected at the beginning of a TCC signal started during a blanking period 304 is highly unlikely to capture the myocardial tissue.

In the example of the receiving device being pacemaker 100 having sensing circuit 174, control circuit 170 may apply a post-sense or post-pace blanking period in response to detecting an intrinsic cardiac event or delivering a pacing pulse. Since both pacemaker 100 and ICD 14 (or ICD 214) may be configured to sense cardiac electrical signals from heart 8, and may be configured to detect pacing pulses delivered by another co-implanted device, both cardiac event detectors 85 and 173 of the transmitting and receiving devices, respectively, may be in a blanking period at the same time or at least during overlapping time periods. As such, by starting transmission of at least the first beacon signal 312 of a new transmission session during a blanking period 304, sensing circuitry of other co-implanted devices configured to detect cardiac electrical signals may also be in a blanking period, reducing the likelihood of low frequency interference with cardiac event detection by other sensing circuits during AC coupling capacitor charging. The blanking period applied to sensing circuit 174 by control circuit 170 is applied to cardiac event detector 173 to prevent oversensing of non-cardiac events during the blanking period. The blanking period is not applied to TCC signal detector 175, which may be operating in a polling mode including beacon search periods 320 and enabled to detect a beacon signal, even during a blanking period applied to cardiac event detector 173.

Beacon signal 312 may include a single tone at the unmodulated carrier signal frequency, e.g., 100 kHz and may be transmitted for 100 ms, 200 ms, 500 ms, 1 second, 2 seconds, or even up to 8 seconds. In other examples the beacon signal 312 may vary between two or more tones within a range of the carrier signal. For instance, the beacon signal 312 may be an FSK signal modulated between two different frequencies to transmit beacon signal 312 having a pre-defined frequency signature that is detected by the TCC signal detector. An FSK modulated beacon signal is described in U.S. Pat. Application No. 62/591,813, incorporated herein by reference in its entirety.

The TCC signal detector of the receiving device, e.g., TCC signal detector 175 of pacemaker 100 or a TCC signal detector included in pressure sensor 50, is configured to detect the beacon signal frequency and compare the frequency to detection criteria. The TCC signal detector may include a comparator and counter configured to count pulses, e.g., by counting zero crossings, edges or other features of the voltage signal received at the receiving electrode vector, and comparing the count to a beacon detection threshold value. In other examples, the TCC signal detector of the receiving device may include a phase locked loop (PLL) that detects the frequency of the voltage signal at the receiving electrode vector. The frequency signal output of the PLL may be compared to the expected beacon signal frequency or frequency pattern.

The peak-to-peak amplitude of the carrier signal used to transmit a beacon signal 312 may be greater than the peak-to-peak amplitude of the carrier signal during transmission of data packets 330. The greater peak-to-peak amplitude of the beacon signal 312 may increase the likelihood of the beacon signal being detected by the receiving device. In other examples, the peak-to-peak amplitude of the carrier signal transmitted as a beacon signal is the same as the peak-to-peak amplitude of the modulated carrier signal during data packet transmission.

The receiving device controls the TCC signal detector, e.g., TCC detector 175, to operate in a polling mode until a beacon signal is detected. The polling mode includes beacon search periods 320 scheduled at polling interval 322. Polling interval 322 may be a pre-determined time interval, e.g., from 0.5 seconds to 8 seconds. In other examples, the polling interval 322 may be variable, for example as generally disclosed in the above-incorporated U.S. Pat. Application No. 62/591,810 (Reinke, et al.).

The duration of the beacon search period 320 may be less than, equal to or greater than the beacon signal 312 in various examples. For instance, with no limitation intended, the beacon signal 312 may be approximately 8 ms to 150 ms long. The beacon search period 320 may be 0.4 to 4 ms long. In other examples, the beacon signal may be up to one second long, up to four seconds long, or even up to eight seconds long. The beacon signal transmission may be suspended if a therapy such as a pacing pulse is scheduled for delivery, e.g., by therapy circuit 83. Transmission of a suspended beacon signal may be resumed after delivery of the pacing pulse. The duration of the beacon search period 320 may be any portion of the duration of the beacon signal 312.

In FIG. 8, the first, earliest beacon search period 320 only partially overlaps with the first beacon signal 312 of wakeup mode 310. If the overlap of beacon search period 320 and beacon signal 312 is too short, beacon detection criteria applied by the receiving device may not be met, and beacon signal 312 may go undetected.

In the example shown, the first (leftmost) beacon signal 312 goes undetected. The second beacon search period 320 occurs during a later beacon signal 312. Beacon signal detection criteria may be reached during the beacon search period 320, e.g., a threshold number of carrier frequency cycles, a threshold number of pairs of alternating frequencies of an FSK modulated beacon signal (as further described below), or a threshold number and/or pattern of phase shifts of a BPSK modulated beacon signal. The receiving device TCC signal detector may generate a beacon detection interrupt signal 324 that is passed to the control circuit of the receiving device, e.g., control circuit 170. The control circuit may end the polling mode of the receiving device and switch to a communication receiving mode to enable reception of data packets 330 by the TCC signal detector.

In the example shown, the receiving device may include a TCC transmitter that is controlled to transmit an acknowledgement signal 328 back to the transmitting device to confirm beacon signal detection and that the receiving device is waiting to receive data packet transmissions. The acknowledgement signal 328 may be transmitted after a delay period 326 to ensure that the transmitting device is no longer transmitting the beacon signal 312 and has switched to a receiving period 314 and is capable of receiving the acknowledgement signal. Acknowledgement signal 328 may be the carrier signal transmitted for a predetermined time interval, e.g., 10 ms or less. The TCC signal transmission techniques disclosed herein are described in the context of a transmitting device transmitting beacon signals and data packets to a receiving device. However, it is to be understood that the TCC signal transmission techniques may be used by the receiving device in generating and transmitting the acknowledgment signal 328 as well.

Beacon signal 312 may be transmitted multiple times during a cardiac cycle or over more than one cardiac cycle. In other examples, each beacon signal 312 may be followed by an OPEN command signal transmitted to the receiving device. The receiving device may detect the beacon signal and switch to a data receiving mode. Upon receiving the subsequent OPEN command signal, the receiving device may transmit an acknowledgement signal back to the transmitting device to confirm to the transmitting device that the TCC signal detector is powered on and ready to receive data transmissions.

During the receiving period 314, the transmitting device enables TCC receiver 87 to detect the acknowledgement signal 328, e.g., by powering the TCC receiver 87 to enable the various filters, amplifiers, comparators, phase locked loop, or other circuitry to receive and detect the acknowledgement signal 328. TCC receiver 87 may generate an acknowledgement detect signal 316 to control circuit 80. Control circuit 80 switches the transmitting device from the wakeup mode 310 to a data transmission mode 311 during which the data packets 330 are transmitted.

In the example shown, not all beacon signals 312 and the data packet 330 are started during a blanking period 304. The first (leftmost) beacon signal 312 of a TCC transmission session may be started during a blanking period 304 to ensure that any low frequency artifact is blanked during charging of the AC coupling capacitor 96. Subsequent TCC signals transmitted during the same TCC transmission session, such as multiple beacon signals 312 and/or one or more data packets 330, may or may not start during a blanking period 304. In some examples, voltage holding circuit 98 may be enabled to hold the AC coupling capacitor 96 at the established DC voltage between consecutively transmitted TCC signals, eliminating the need to start each TCC signal during a blanking period 304 after the DC voltage is established on the AC coupling capacitor 96. In other examples, if the time between TCC signals is relatively short, e.g., one second or less, leakage current causing AC coupling capacitor 96 to discharge between TCC signals may be minimal such that the AC coupling capacitor 96 remains substantially charged at the DC operating voltage between TCC signal transmissions within a transmission session. Only the first beacon signal 312 is transmitted during blanking period 304 to initially establish the DC operating voltage on the AC coupling capacitor 96.

According to the TCC signal transmission techniques disclosed herein, each beacon signal 312 and each data packet 330 is started with a starting pulse having less than half of the carrier signal half-cycle charge to avoid the DC voltage shift that may occur if the starting pulse is the full half-cycle charge. In one example, each beacon signal 312 and each data packet 330 that is started with a starting pulse having a net charge that is half of the half-cycle charge (i.e., one-quarter the full cycle charge) of the carrier signal and is ended with an ending pulse having a net charge that is half of the half-cycle charge (i.e., one-quarter the full cycle charge). The starting and ending pulses may be transmitted with a one-quarter of the cycle length of the carrier frequency (as shown in FIG. 7B) or with one-quarter of the peak-to-peak amplitude to produce a pulse with one-half of half cycle charge of carrier signal. Alternatively, the one-quarter the cycle charge may be obtained via a combination of the fraction or percentage of the cycle length and the fraction or percentage of amplitude of the starting and ending pulses (e.g., X % of the half-cycle length and Y % of the amplitude, X and Y being less than 100). Moreover, the starting and ending pulses may have some other fraction or percentage of the half-cycle charge other than one-quarter. For example, the starting and ending pulses may have between one-third and two-thirds of the half-cycle charge, i.e., between one-sixth and one-third of the full cycle charge. The starting and ending pulses may have the same fraction of the half-cycle charge or different fractions of the half-cycle charge. For instance, the starting pulse may have one-quarter of the cycle charge and the ending pulse may have one-third of the cycle charge. For purpose of illustration, the techniques of this disclosure will be described in the context of starting and ending pulses having half of the half-cycle charge (i.e., one-quarter the full cycle charge) of the carrier signal throughout the remainder of this disclosure. However, it should be clear to one of skill in the art that starting and ending pulses may have some other fraction or percentage of the half-cycle charge other than one-quarter.

In the example of FIG. 9, the first beacon signal 312 is transmitted during blanking period 304 to enable the DC voltage to be established on the AC coupling capacitor 96 during blanking of sensing circuit 86. As such, the first (leftmost) beacon signal 312 of a transmission session may be transmitted with unmodified starting and ending pulses. Each starting and ending pulse correspond to half of the carrier signal cycle, each having a pulse width that is half the carrier frequency cycle length in duration and having an amplitude that is half of the peak-to-peak amplitude of the carrier signal. Thus, each of the starting and ending pulses have a net charge of half of the cycle charge. During blanking period 304, any DC voltage shift caused by the unmodified carrier signal cycles at the start and end of the TCC signal, e.g., as shown in FIG. 7A, will not be detected as a cardiac event by cardiac event detector 85. As such, in some examples, all TCC signals, including beacon signals 312 and data packets 330 transmitted during a blanking period 304 may be transmitted with a starting and ending pulse each having a net charge that is half of the full cycle charge of the carrier signal. All TCC signals transmitted outside a blanking period 304 may be transmitted with starting and ending pulses having a net charge of half of the half cycle charge of the carrier signal. Starting and ending TCC signals transmitted during a blanking period 304 (such as the first, leftmost beacon signal 312) with pulses having half of the half cycle charge is optional.

Figure 10:
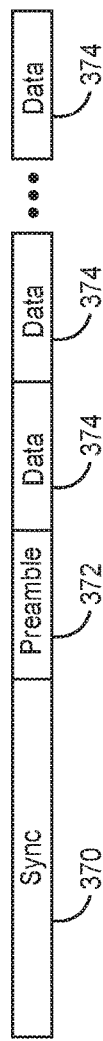
FIG. 10 is a diagram of a data packet that may be transmitted during the data transmission mode by the TCC transmitting device according to one example.

FIG. 10 is a diagram of a data packet 330 that may be transmitted during the data transmission mode 311 by the transmitting device according to one example. Data packet 330 may include multiple fields 370, 372 and 374 transmitted using a carrier signal and BPSK modulation. A synchronization field 370 is transmitted as the first field at the unmodulated carrier signal frequency, e.g., 100 kHz, to provide a carrier lock for the demodulation by the TCC signal detector of the receiving device. The synchronization field 370 may include a predetermined number of carrier frequency cycles or bits, e.g., with eight cycles per bit. The synchronization field 370 may be between 128 and 256 cycles long in some examples. Synchronization field 370 may be started with a first, starting pulse having a net charge that is half of the half cycle charge of the carrier signal to avoid introducing a DC voltage shift at the input to electrical signal sensing circuitry included in the transmitting device or a receiving device, intended or unintended, in the IMD system.

The carrier signal transmitted during the synchronization field 370 is modulated during the preamble and data fields 372 and 374 according to a binary coded input signal, which may be produced by a modulator included in controller 91. The preamble field 372 may follow the synchronization field 370 and may be encoded to communicate the type of packet being transmitted and the packet length, e.g., the number of data fields. The preamble field 372 may also include a key code to provide bit sample timing to the receiving device, an acknowledgment request bit, source and/or destination address bits, or other bits or bytes that may normally be included in a header or preamble field 372.

Data fields 374 include the information being communicated to the receiving device, which may include commands to perform therapy delivery or signal acquisition, requests for data, control parameter settings to be used by the receiving device for sensing physiological signals and/or delivering a therapy, or numerous other types of encoded information that enable coordination of the IMD system in monitoring the patient and delivering therapy. Each data field 374 may include one byte and each byte may be a predetermined number of bits, e.g., 8 bits, 9 bits, 13 bits or other predetermined number, representing a stream of digital values. Each data packet 330 may include 1 to 256 data fields or bytes. In some examples, the data packet 330 may be terminated with a cyclic redundancy check (CRC) field to enable the receiving device to perform an error check. While a particular example of a data packet 330 (or datagram when transmitted without incorporating acknowledgment requests and receipts) is shown in FIG. 10, numerous data frame structures including various fields may be conceived according to a particular clinical application and IMD system that utilize ramp on and ramp off signals as described herein.

The last data field 374 of each data packet 330 is ended with an ending pulse having a net charge that is equal to half of the half cycle charge of the carrier signal. As such, each data packet 330 may start and end with a pulse with a net charge that is half of the half cycle charge to avoid DC voltage shifts at the start and end of a data packet 330 that may lead to false cardiac event detection by cardiac event detector 85.

Figure 11:
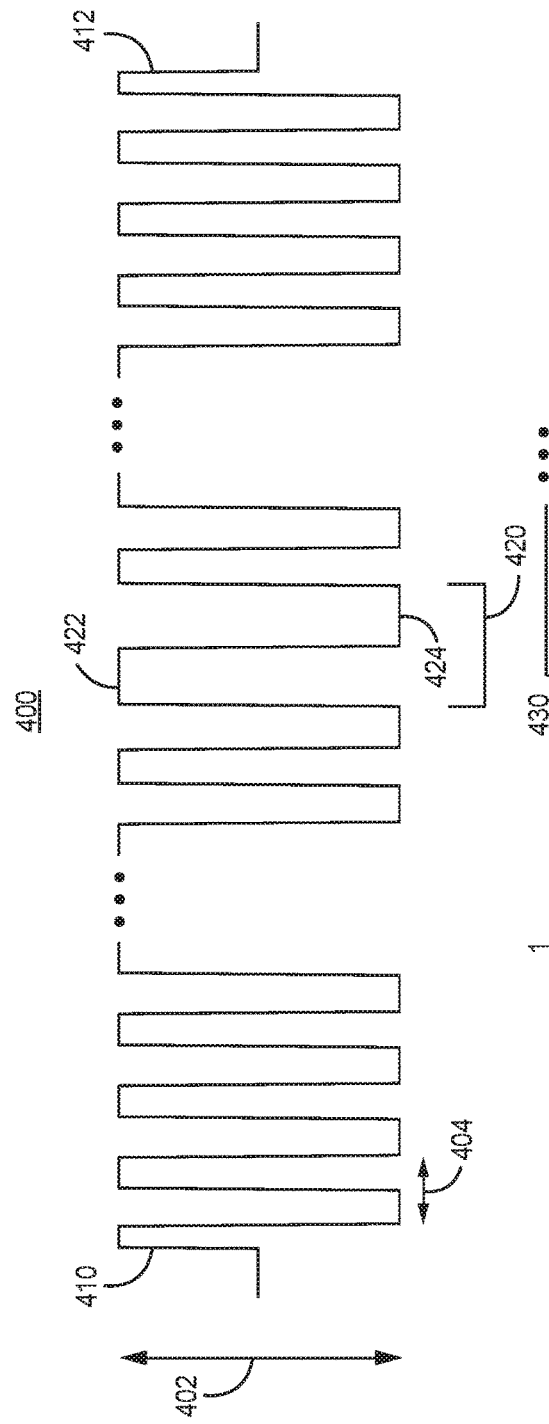
FIG. 11 is a conceptual diagram of a portion of a data packet, e.g., the data packet of FIG. 10, according to one example.

FIG. 11 is a conceptual diagram 400 of a portion of a data packet, e.g., data packet 330 of FIG. 10, according to one example. The TCC signal 400 includes a carrier signal having a carrier frequency cycle length 404, e.g., 10 microseconds for a 100 kHz carrier frequency, and a peak-to-peak current amplitude 402, e.g., 10 mA peak-to-peak. The voltage at the transmitting electrode vector is dependent on the injected current and electrode impedance, e.g., 5 Volts peak-to-peak for a 10 mA peak-to-peak current signal and 500 ohms impedance of the transmitting electrode vector. In other examples, the current amplitude is between 1 mA and 30 mA or more. The received voltage signal at the receiving electrode vector may range from less than 150 microvolts peak-to-peak up to 30 millivolts peak-to-peak for effective communication. For instance, the received voltage signal may be approximately 1 millivolt peak-to-peak.

The peak-to-peak current amplitude 402 may be adjustable based on patient sensation, programmed sensitivity of the cardiac event detector 85, carrier frequency of the TCC signal, proximity and relative orientation of the transmitting and receiving devices and other factors. The peak-to-peak amplitude 402 may be relatively higher without detection by cardiac event detector 85 for a given programmed sensitivity setting of the cardiac event detector 85 using the techniques disclosed herein as compared to a TCC signal having normal, half-cycle length starting and ending pulses which may cause DC voltage shifts that interfere with cardiac event detector 85.

Controller 91 of TCC transmitter 90 controls the drive signal circuit 92 and/or polarity switching circuit 94 to transmit a starting pulse 410 having one-half of the half cycle charge of the carrier signal. In this example, starting pulse 410 has one-quarter of the carrier signal cycle length 404 and an amplitude that is half of the peak-to-peak amplitude 402. In the illustrative example of a 100 kHz carrier frequency, starting pulse 410 is 2.5 microseconds, and the carrier signal cycle length 404 is 10 microseconds. However, controller 91 of TCC transmitter 90 may control the drive signal circuit 92 and/or polarity switching circuit 94 to achieve the half of the half cycle charge by adjusting the amplitude of the carrier signal or a combination of the amplitude and the cycle length of the carrier signal. The starting pulse 410 may be the first pulse of a synchronization field 370 as shown in FIG. 10.

Controller 91 controls the drive signal circuit 92 and/or polarity switching circuit 94 to end transmission of TCC signal 400 with an ending pulse 412 that is half of the half-cycle charge, e.g., one-quarter of the cycle length 404 with an amplitude equal to half of the peak-to-peak amplitude. Both the starting and the ending pulses 410 and 412 may have the same polarity or the opposite polarity. The ending pulse 412 may be the last pulse of the last data field 374 of the data packet 330 of FIG. 10.

In the example shown, only one single starting pulse 410 having half of the half cycle charge and only one single ending pulse 412 having half of the half cycle charge are delivered during transmission of TCC signal 400. All other cycles of the modulated carrier signal, besides the starting and ending pulses 410 and 412 and excluding pulses included in a phase shift 420 (described below) of a BPSK modulated signal, are controlled to have the half cycle charge and alternate in polarity. As such, the starting pulse 410 may be followed consecutively by and continuously with multiple carrier signal cycles. Controller 91 controls drive signal circuit 92 and/or polarity switching circuit 94 to transmit multiple alternating polarity pulses of the carrier signal consecutively following and continuously with (no interruption in signal transmission) starting pulse 410. The multiple pulses of the carrier signal following starting pulse 410 are transmitted as a continuous signal at the carrier frequency with alternating polarity pulses each having a pulse width equal to approximately half of the carrier frequency cycle length 404 and an absolute amplitude equal to approximately half of the peak-to-peak amplitude 402.

Ending pulse 412 may consecutively follow and be continuous with multiple preceding carrier signal cycles. Controller 91 controls drive signal circuit 92 and/or polarity switching circuit 94 to transmit multiple alternating polarity pulses of the carrier signal consecutively preceding and continuously with (no interruption in signal transmission) ending pulse 412. The multiple pulses of the carrier signal preceding ending pulse 412 are transmitted as a continuous signal at the carrier signal frequency with the alternating polarity pulses each having a pulse width equal to approximately half of the carrier frequency cycle length 404 and an absolute amplitude equal to approximately half of the peak-to-peak amplitude 402. While a single starting pulse 410 and a single ending pulse 412 are shown in FIG. 11, it is contemplated that TCC signal 400 may include one or more consecutive starting pulses 410 and one or more consecutive ending pulses 412 respectively preceding and following multiple carrier signal cycles delivered continuously and consecutively with the respective preceding starting pulse(s) 410 and ending pulse(s) 412.

Controller 90 may be configured to control drive signal circuit 92 and/or polarity switching circuit 94 to modulate the carrier signal using BPSK according to an input digital signal 430. Input digital signal 430 may be produced by controller 91 for encoding communication data on the carrier frequency signal. Alternatively, input digital signal 430 may be produced by a modulator of RF telemetry circuit 88 and passed to controller 91 by control circuit 80. Input digital signal 430 may be used to control polarity switching circuit 94 to control the timing of switches used to switch the polarity of the carrier signal to cause a phase shift of the carrier signal according to BPSK modulation. Input digital signal 430 has a digital low "0" value followed by a digital high "1" value. Controller 90 controls the polarity switching circuit 94 to produce a phase shift 420. The intended receiving device, e.g., pacemaker 100 or pressure sensor 50, is configured to detect the phase shift 420 and set the bit value of a stream of digital bits to a digital "1" in response to detecting the phase shift 420. A bit value of zero prior to the phase shift 420 is followed by a bit value of one in a stream of bits produced by a demodulator of TCC signal detector 175 and passed to control circuit 170 (e.g., of pacemaker 100 as shown in FIG. 3B) for decoding.

The phase shift 420 is a positive 180-degree phase shift of the carrier signal and includes a first pulse 422 having a three-quarter cycle length pulse width and a second pulse 424 having a three-quarter cycle length pulse width and opposite polarity from the first pulse 422. The combination of the two three-quarter cycle length pulses produces a net positive 180-degree phase shift. The two three-quarter cycle length pulses 422 and 424 of opposite polarity cause a 180-degree phase shift of the TCC signal 400 while balancing the injected charge during the phase shift 420.

The polarity switching circuit 94 may be controlled to switch the polarity of the drive current signal received from drive signal circuit 92 after three-quarters of the carrier frequency cycle length for two consecutive pulses to generate phase shift 420. The duration of the phase shift is 150% of the carrier cycle length 404 resulting in a net positive 180-degree phase shift. Alternatively, controller 91 may control the polarity switching circuit 94 to switch the polarity of the current signal received from drive signal circuit 92 after one-quarter of the carrier signal cycle length 404 for two consecutive pulses of opposite polarity to produce two, charge-balanced pulses that shift the phase a net negative 180 degrees. The duration of the phase shift in this case is 50% of the carrier frequency cycle length 404 resulting in a net negative 180-degree phase shift.

In another example, a positive 90-degree phase shift may be achieved by controlling polarity switching circuit to generate two consecutive pulses each having a pulse width that is five-eighths of the carrier signal cycle length 404. In various examples, phase shift 420 may include two pulses of opposite polarity having equal pulse widths that are a selected percentage of the carrier frequency cycle length 404 to achieve a net positive or negative phase shift up to 360 degrees. The two pulses of phase shift 420 deliver a balanced charge to achieve a net zero DC voltage shift at the receiving electrode vector. The TCC signal detector 175 of the receiving device includes a demodulator configured to detect each phase shift 420 to produce a bit stream of digital values that switches between high and low values in response to each phase shift detection.

TCC signal 400 includes a single phase shift 420 in the example shown to illustrate the phase shift technique disclosed herein. It is recognized, however, that TCC signal 400 may include multiple phase shifts to encode data included in each field of the data packet 330, e.g., within preamble field 372 and each data field 374 shown in FIG. 10. Having at least two phase shifts in a TCC signal 400 may reduce interference with cardiac event detector 85 compared to a TCC signal having a single phase shift. As can be seen in FIG. 11, the encoded data may be transmitted during a data packet by continuously transmitting the carrier signal without interruption while controlling the drive signal circuit 92 and the polarity switching circuit 94 to shift the phase of the carrier signal using charge balanced phase shift pulses 422 and 424.

Figure 12:
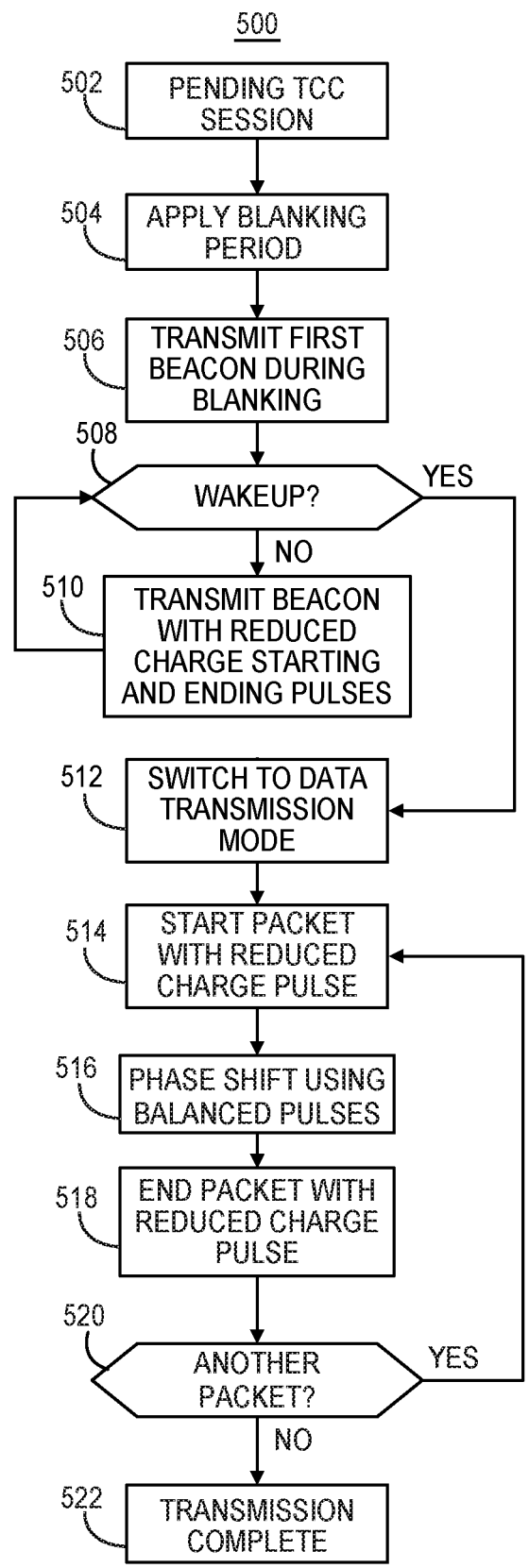
FIG. 12 is a flow chart of a method for transmitting TCC signals by an IMD according to one example.

FIG. 12 is a flow chart 500 of a method for transmitting TCC signals by an IMD according to one example. The process of flow chart 500 may be performed by TCC transmitter 90 under the control of control circuit 80 (FIG. 5). In the description provided, the transmitting IMD is ICD 14 or ICD 214, however pacemaker 100, pressure sensor 50 or another IMD may include TCC transmitter 90 and perform the transmission methods of FIG. 12.

At block 502, the ICD control circuit 80 determines that a TCC transmission session is pending. A transmission session may include one or more beacon signals and one or more data packets as described above. At least the first beacon signal of the transmission session may be transmitted during a blanking period applied to the sensing circuit of the transmitting device. In the case of ICD 14 or ICD 214 including a cardiac event detector 85, control circuit 80 may apply a blanking period to sensing circuit 86 at block 504 and control TCC transmitter 90 to initiate at least the first beacon signal of the transmission session at block 506 during the blanking period. The beacon signal may be a modulated or unmodulated carrier signal, e.g., an FSK modulated carrier signal. The first beacon signal may or may not be transmitted with starting and ending pulses having half of the half cycle charge of the carrier signal. In other examples, control circuit 80 may not include a blanking period, in which case the first beacon signal may be transmitted with starting and ending pulses having half of the half cycle charge of the carrier signal.

At the start of a transmission session, the early cycles of the carrier signal establish a DC voltage across the AC coupling capacitor 96. During this time, which may be 10 ms, 50 ms, 100 ms, or even up to 200 ms or more, a low frequency current may be injected into the body tissue conductive pathway via the TCC transmitting electrode vector. The low frequency current may cause interference with the cardiac event detector 85 (or other electrophysiological sensing circuits or impedance monitoring circuits of the transmitting device or other implanted devices). By starting the first beacon signal of each transmission session during a blanking period, the DC voltage may be established on the AC coupling capacitor 96 mostly or entirely during the blanking period when the sensing circuit 86 is blanked and relatively immune to the low frequency artifact.

In some examples, the TCC transmission session is initiated at block 506 by starting transmission of the first beacon signal of the transmission session during an automatic blanking period that is applied to the cardiac event detector 85 by control circuit 80 based on the timing of sensed cardiac events and/or delivered electrical stimulation pulses. Control circuit 80 may be configured to identify a cardiac event, sensed or pace, apply a blanking period to the sensing circuit 86 in response to identifying the cardiac event, and control TCC transmitter 90 to start transmission of the first beacon signal during the blanking period. In other examples, control circuit 80 may apply a communication blanking period to cardiac event detector 85 independent of the timing of cardiac electrical events, sensed or paced. In some cases, a communication blanking period may be applied to sensing circuit 86 by control circuit 80 during the cardiac cycle between sensed or paced events. The communication blanking period may be applied by control circuit 80 to enable TCC signal transmission to be started at any time during the cardiac cycle, without waiting for an automatic post-sense or post-pace blanking period.

A communication blanking period may be shorter or longer than the automatic post-sense or post-pace blanking period. For example, a communication blanking period may be in the range of 10 ms to 200 ms and may depend on the programmed sensitivity of the cardiac event detector 85 and the duration of low frequency interference at the start of TCC beacon signal transmission. The maximum duration of the communication blanking period may be limited based on the particular clinical application. For example, in the cardiac monitoring and therapy delivery IMD systems 10 and 200 disclosed herein, the maximum time that cardiac event detector 85 is blinded to detecting cardiac events may be 200 ms or less. In non-cardiac applications, e.g., monitoring muscle or nerve signals, longer or shorter communication blanking intervals may be applied.

At block 508, the transmitting device may wait for an acknowledgement signal from the receiving device. If no acknowledgement signal is received, controller 91 may control the drive signal circuit 92 and/or polarity switching circuit 94 to transmit another beacon signal at block 510. The second beacon signal may be transmitted outside a blanking period. Controller 91 controls the drive signal circuit 92 and polarity switching circuit to transmit the second beacon signal at block 510 with a starting and ending pulse each having less than a half cycle charge of the carrier signal. For example, each of the starting pulse and the ending pulse of the second beacon signal may be transmitted with one-fourth the peak-to-peak amplitude of the carrier signal or one-fourth of the cycle length of the carrier signal so that each of the starting and ending pulses have one-fourth of the charge of one full carrier signal cycle.

One or more beacon signals may be repeated having reduced charge starting and ending pulses, and may be transmitted outside a blanking period, until an acknowledgement signal is received from the intended receiving device. If the acknowledgment signal is received, controller 91 may switch the transmitter 90 from the wakeup mode to the data transmission mode at block 512.

At block 514, the first data packet of the transmission session is transmitted. Controller 91 controls drive signal circuit 92 and/or polarity switching circuit 94 to generate a first pulse of the data packet with a charge that is less than the half cycle charge of the carrier signal, e.g., half of the half cycle charge as described above, to avoid or minimize a DC voltage shift at a receiving electrode vector at the onset of the data packet.

During transmission of the data packet, controller 91 may encode data on the carrier signal by FSK, PSK or other modulation methods. According to one example, transmitter 90 is configured to transmit data using BPSK modulation. One or more phase shifts may occur during the transmitted data packet. At block 516, each phase shift for BPSK modulation of the carrier signal is performed by controlling polarity switching circuit 94 to shift the phase using balanced positive and negative pulses of the TCC signal. For example, instead of one longer positive or negative pulse to shift the phase, two pulses, one positive and one negative may be used, each having an equal pulse width defined as some portion of the carrier frequency cycle length to produce the desired net phase shift. For example, both a positive- and negative-going pulse of the phase shift may be greater than half of the cycle length of the carrier frequency to produce a positive phase shift, or both the positive- and negative-going pulses of the phase shift may be less than half of the cycle length to produce a negative phase shift. As described above, the controller 91 may control the drive signal circuit 92 and polarity switching circuit to modulate the carrier signal with a positive phase shift of 180 degrees by generating a phase shift that includes two three-quarters cycle length pulses of opposite polarity. In other examples, block 516 may include other types of modulation techniques, such as FSK.

At block 518, TCC transmitter 90 terminates the data packet with an ending pulse having a net charge that is half of the half cycle charge of the carrier signal. The ending pulse may have half of the carrier signal peak-to-peak amplitude and a pulse width that is one-quarter of the carrier frequency cycle length for example. In another example, the ending pulse may have one-quarter of the peak-to-peak amplitude and a pulse width that is one-half of the carrier frequency cycle length. By starting and ending each data packet during the TCC transmission session with a pulse that injects half of the half cycle charge, a DC voltage shift at the receiving electrode vector is minimized or avoided. The cardiac event detector 85 is less likely to falsely detect a cardiac event from the TCC signal than if the packet begins and/or ends with a normal, half-cycle length pulse of the carrier signal.

If the TCC transmission session includes another data packet, as determined at block 520, the process returns to block 514. Each data packet may be delivered with a starting and ending pulse having one-half of the half cycle charge of the carrier signal. Each phase shift in each data packet includes two, balanced pulses of opposite polarity, e.g., two three-quarter cycle length pulses having opposite polarity. A blanking period may or may not be applied at the start of each data packet. As shown in FIG. 9, a blanking period may be required only upon a "cold start" of the TCC transmission session, at the start of the first beacon signal. All subsequent TCC signals during the transmission session, which may include one or more subsequent beacon signals as needed and one or more subsequent data packets, are not required to start within a blanking period. All subsequent TCC signals, however, may be transmitted but with starting and ending pulses each having a net charge that is half of the half cycle charge of the carrier signal to avoid DC voltage shifts at an intended or unintended receiving electrode vector.

The TCC transmission session is complete at block 522 when all data packets in the TCC transmission have been transmitted. The control circuit 80 of the transmitting device may switch the transmitter 90 to a low power, sleep state until the next TCC transmission session. In some cases, the first beacon signal of the next TCC transmission session may not be required to be started during a blanking period. If the next TCC transmission session occurs relatively soon, e.g., within one minute of the immediately preceding TCC transmission session, the AC coupling capacitor 96 may still be charged to the DC operating voltage. The first beacon signal of the next TCC transmission session may be started outside a blanking period and include starting and ending pulses each having a net charge that is half of the half cycle charge of the carrier signal to avoid DC voltage shifts at a receiving electrode vector.

Figure 13:
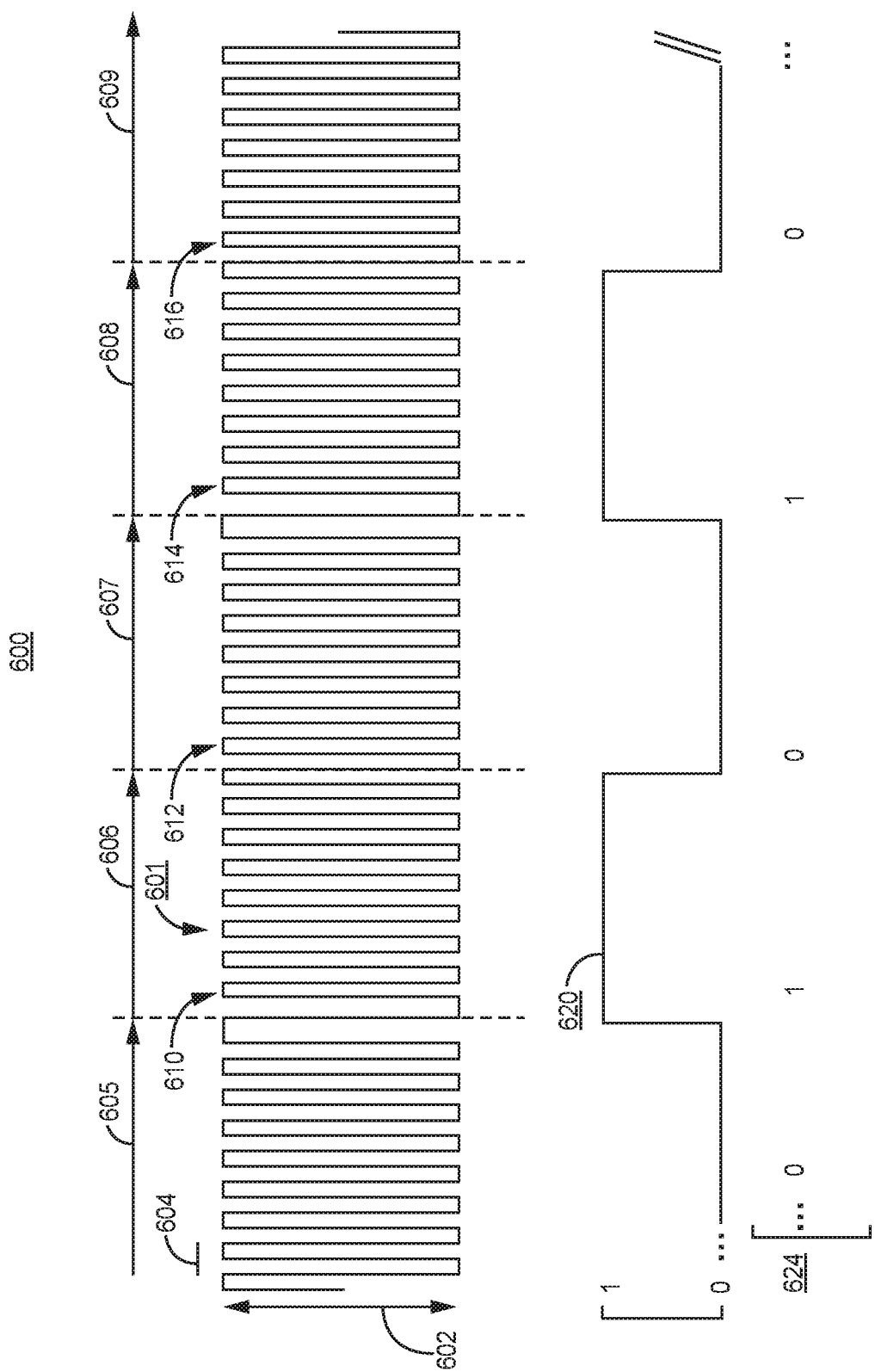
FIG. 13 is a conceptual diagram of a portion of one data byte that may be included in a data packet transmitted as a TCC signal.

FIG. 13 is a conceptual diagram of a portion of one data byte 600 that may be included in a preamble field 372 or a data field 374 of packet 430. Each data byte 600 may be transmitted as the carrier signal 601 modulated using BPSK. The carrier signal 601 has a peak-to-peak amplitude 602 and carrier frequency that is defined by the carrier frequency cycle length 604. The carrier signal 601 has a positive polarity at half the peak-to-peak amplitude 602 during one half of the carrier frequency cycle length 604 and negative polarity at half the peak-to-peak amplitude 602 during the other half of the carrier frequency cycle length 604.

An input digital signal 620 may be generated by transmitter controller 91 to control drive signal circuit 92 and/or polarity switching circuit 94 of transmitter 90 (all shown in FIG. 6) to control modulation of the carrier signal 601 during transmission of data byte 600. Each bit 605-609 of the transmitted TCC signal data byte 600 is encoded by delivering a predetermined number of carrier frequency cycles per bit and a phase shift between consecutive bits that is controlled according to input digital signal 620. In the example shown, each bit 605-609 includes eight carrier frequency cycles 604. The bit value is encoded by controlling drive signal circuit 92 and/or polarity switching circuit 94 to produce either a zero phase shift between bits or a phase shift between bits. Each phase shift 610 and 614 in the example of FIG. 13 includes a pair of opposite polarity, charge balanced pulses as described in conjunction with FIG. 11. No phase shift between bits may correspond to a digital "0" in the bit stream, and a phase shift may correspond to a digital "1" in the bit stream.

To illustrate, the first bit 605 may be a digital "0" and is followed by a phase shift 610 leading into the next bit 606. The phase shift 610 is a positive 180-degree phase shift produced by two consecutive three-quarter cycle length pulses having opposite polarity. The TCC signal detector 175 of the receiving device that is locked into the frequency of the carrier signal 601 is configured to detect the phase shift 610. In response to detecting the phase shift 610, the TCC signal detector 175 outputs a digital "1" in digital output signal 624 that is passed to the control circuit of the receiving device for decoding. Bit 606 is followed by no phase shift 612 according to the digital input signal 620 which changes from a digital "1" to a digital "0." The TCC signal detector 175 of the receiving device detects no phase shift and produces a digital "0" for bit 607 in response to detecting no phase shift after the eight cycles of bit 606.

The next bit 607 is followed by a 180-degree positive phase shift 614 in accordance with the change from a digital "0" to a digital "1" in the input digital signal 620. The phase shift 614 includes two three-quarter cycle length pulses of opposite polarity and is detected by the TCC signal detector 175. The bit value in the output digital signal 624 changes from "0" to "1" for bit 608. The eight cycles of bit 608 are followed by no phase shift 616, in accordance with a change from "1" to "0" in the input signal 624. In response to no phase shift detection, the TCC signal detector 175 produces a digital "0" in the output digital signal 624 corresponding to the last bit 609. The last five bits of data byte 600 are represented in FIG. 13, however it is recognized that data byte 600 may include 2, 4, 8, 16, or other predetermined number of bits. The last four bits 606-609 may represent a nibble (four bits) of byte 600 including at least 8 bits (an octet) in a hexadecimal encoding scheme.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or component for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a system including a device having a TCC transmitter configured to transmit TCC signals has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

The invention claimed is:

1. A device comprising:
a housing; and
a tissue conduction communication (TCC) transmitter enclosed by the housing and configured to transmit one or more TCC signals of a TCC communication session via a transmitting electrode vector; and
a controller configured to control the TCC transmitter to:
generate a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length,
transmit a starting pulse of a first one of the TCC signals having a net charge that is a fraction of the full cycle charge, the fraction being less than one-half,
transmit a plurality of the alternating polarity pulses of the carrier signal of the first TCC signal consecutively following the starting pulse as a continuous signal, each one of the plurality of alternating polarity pulses having a net charge of one-half of the full cycle charge, and
modulate the first one of the TCC signals by modulating the alternating polarity pulses of the carrier signal.

2. The device of claim 1, wherein the fraction is between one-sixth and one-third the full cycle charge.

3. The device of claim 1, wherein the fraction is one-quarter of the full cycle charge.

4. The device of claim 1, wherein the controller is configured to control the TCC transmitter to transmit the starting pulse of the first TCC signal having the net charge that is the fraction of the full cycle charge by transmitting the starting pulse with a pulse width that is a fraction of the carrier frequency cycle length.

5. The device of claim 1, wherein the controller is configured to control the TCC transmitter to transmit the starting pulse of the first TCC signal having the net charge that is the fraction of the full cycle charge by transmitting the starting pulse with a pulse amplitude that is a fraction of a peak-to-peak amplitude of the carrier signal.

6. The device of claim 1, wherein the controller is configured to control the TCC transmitter to transmit an ending pulse of the first TCC signal consecutively following the plurality of alternating polarity pulses of the carrier signal and having a net charge that is between one-sixth and one-third the full cycle charge.

7. The device of claim 1, further comprising a sensing circuit enclosed by the housing and configured to receive a cardiac electrical signal via a plurality of electrodes coupled to the sensing circuit.

8. The device of claim 7, further comprising a control circuit configured to apply a first blanking period to the sensing circuit, wherein
the controller is further configured to control the TCC transmitter to:
transmit a second one of the TCC signals of the TCC transmission session during the first blanking period, a starting pulse of the second one of the TCC signals having a net charge that is one-half of the full cycle charge.

9. The device of claim 1, wherein the controller is further configured to modulate the carrier signal by controlling the TCC transmitter to transmit the first TCC signal with at least one phase shift of the carrier signal, each phase shift comprising a first phase shift pulse having a first percentage of the carrier frequency cycle length and a second phase shift pulse having a second percentage of the carrier frequency cycle length equal to the first percentage, the first phase shift pulse and the second phase shift pulse being opposite in polarity.

10. The device of claim 9, wherein the controller is further configured to control the TCC transmitter to generate each of the first phase shift pulse and the second phase shift pulse having three-fourths of the carrier frequency cycle length.

11. The device of claim 1, wherein:
the TCC transmitter comprises an alternating current (AC) coupling capacitor, and
the controller is configured to control the TCC transmitter to transmit the one or more TCC signals by coupling the AC coupling capacitor to the transmitting electrode vector.

12. A method comprising:
generating a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length;
transmitting a starting pulse of a first one of the TCC signals of a TCC communication session having a net charge that is a fraction of the full cycle charge, the fraction being less than one-half;

transmitting a plurality of the alternating polarity pulses of the carrier signal of the first TCC signal consecutively following the starting pulse as a continuous signal, each one of the plurality of alternating polarity pulses having a net charge of one-half of the full cycle charge; and modulating the first one of the TCC signals by modulating the alternating polarity pulses of the carrier signal.

13. The method of claim 12, wherein transmitting the starting pulse comprises transmitting the starting pulse of the first TCC signal having a net charge that is between one-sixth and one-third of the full cycle charge.

14. The method of claim 12, wherein transmitting the starting pulse comprises transmitting the starting pulse of the first TCC signal having a net charge that is one-quarter of the full cycle charge.

15. The method of claim 12, wherein transmitting the starting pulse of the first one of the TCC signals comprises transmitting the starting pulse with a pulse width that is a fraction of the carrier frequency cycle length.

16. The method of claim 12, wherein transmitting the starting pulse of the first one of the TCC signals comprises transmitting the starting pulse with a pulse amplitude that is a fraction of a peak-to-peak amplitude of the carrier signal.

17. The method of claim 12, further comprising transmitting an ending pulse of the first TCC signal consecutively following the plurality of alternating polarity pulses of the carrier signal and having a net charge that is between one-sixth and one-third the full cycle charge.

18. The method of claim 12, further comprising:
receiving a cardiac electrical signal via a plurality of electrodes by a sensing circuit;
applying a blanking period to the sensing circuit;
transmitting a second one of the TCC signals of the TCC transmission session during the blanking period, a starting pulse of the second one of the TCC signals having a net charge that is one-half of the full cycle charge.

19. A non-transitory, computer-readable storage medium comprising a set of instructions which, when executed by a device having a tissue conduction communication (TCC) transmitter, cause the device to:
generate a carrier signal having alternating polarity pulses and a carrier frequency cycle length, wherein each carrier frequency cycle length includes a pair of alternating polarity pulses comprising a first polarity pulse for a first half of the carrier frequency cycle length and a second polarity pulse opposite the first polarity pulse for a second half of the carrier frequency cycle length, each of the first polarity pulse and the second polarity pulse having a net charge of one-half of a full cycle charge of the carrier signal during a full carrier frequency cycle length;
transmit a starting pulse of a first one of the TCC signals of a TCC communication session having a net charge that is between one-sixth and one-third of the full cycle charge;
transmit a plurality of the alternating polarity pulses of the carrier signal of the first TCC signal consecutively following the starting pulse as a continuous signal, each one of the plurality of alternating polarity pulses having a net charge of one-half of the full cycle charge; and
modulate the first one of the TCC signals by modulating the alternating polarity pulses of the carrier signal.

* * * * *